(12) United States Patent
Hunt et al.

(10) Patent No.: US 9,757,235 B2
(45) Date of Patent: Sep. 12, 2017

(54) SPINAL PROGRAMMABLE IMPLANT

(71) Applicant: 4WEB, Frisco, TX (US)

(72) Inventors: Jessee Hunt, Plano, TX (US); Timothy Ganey, Tampa, FL (US)

(73) Assignee: 4WEB, Inc., Frisco, TX (US)

( * ) Notice: Subject to any disclaimer, the term of this patent is extended or adjusted under 35 U.S.C. 154(b) by 0 days.

(21) Appl. No.: 15/057,195

(22) Filed: Mar. 1, 2016

(65) Prior Publication Data
US 2016/0287405 A1    Oct. 6, 2016

Related U.S. Application Data

(63) Continuation of application No. 14/036,974, filed on Sep. 25, 2013, now Pat. No. 9,271,845.
(Continued)

(51) Int. Cl.
*A61F 2/44*     (2006.01)
*A61F 2/28*     (2006.01)
(Continued)

(52) U.S. Cl.
CPC ............. *A61F 2/28* (2013.01); *A61F 2/2803* (2013.01); *A61F 2/30* (2013.01); *A61F 2/30907* (2013.01); *A61F 2/30942* (2013.01); *A61F 2/32* (2013.01); *A61F 2/38* (2013.01); *A61F 2/4202* (2013.01); *A61F 2/4225* (2013.01); *A61F 2/44* (2013.01); *A61F 2/447* (2013.01); *A61F 2/4455* (2013.01); *A61F 2/4465* (2013.01); *A61F 2/4611* (2013.01); *A61F 2002/2835* (2013.01); *A61F 2002/3014* (2013.01); *A61F 2002/3092* (2013.01); *A61F 2002/3093* (2013.01);
(Continued)

(58) Field of Classification Search
CPC .......... A61F 2/44; A61F 2/4455; A61F 2/447
USPC .......................................... 623/1.11–17.167
See application file for complete search history.

(56) References Cited

U.S. PATENT DOCUMENTS 3,840,904 A    10/1974  Tronzo
3,867,728 A    2/1975   Stubstad et al.
(Continued)

FOREIGN PATENT DOCUMENTS

CN    201164511    12/2008
CN    201200499     3/2009
(Continued)

OTHER PUBLICATIONS

"Rapid prototyping enables company to manufacture revolutionary new medical product", accessed at <http://www.newslettersonline.com/user/user.fas/s=63/fp=3/tp=47?T=open_article,565208&P=article>, Oct. 9, 2003. (pp. 1-2).
(Continued)

*Primary Examiner* — Christopher Beccia
(74) *Attorney, Agent, or Firm* — Meyertons, Hood, Kivlin, Kowert & Goetzel, P.C.

(57) ABSTRACT

Various embodiments of implant systems and related apparatus, and methods of operating the same are described herein. In various embodiments, an implant for interfacing with a bone structure includes a web structure, including a space truss, configured to interface with human bone tissue. The space truss includes two or more planar truss units having a plurality of struts joined at nodes. Implants are optimized for the expected stress applied at the bone structure site.

24 Claims, 17 Drawing Sheets

Related U.S. Application Data

(60) Provisional application No. 61/705,403, filed on Sep. 25, 2012, provisional application No. 61/801,597, filed on Mar. 15, 2013.

(51) Int. Cl.
    *A61F 2/46*         (2006.01)
    *A61F 2/32*         (2006.01)
    *A61F 2/38*         (2006.01)
    *A61F 2/42*         (2006.01)
    *A61F 2/30*         (2006.01)

(52) U.S. Cl.
CPC ............ *A61F 2002/3097* (2013.01); *A61F 2002/30143* (2013.01); *A61F 2002/30153* (2013.01); *A61F 2002/30156* (2013.01); *A61F 2002/30158* (2013.01); *A61F 2002/30179* (2013.01); *A61F 2002/30273* (2013.01); *A61F 2002/30275* (2013.01); *A61F 2002/30278* (2013.01); *A61F 2002/30281* (2013.01); *A61F 2002/30283* (2013.01); *A61F 2002/30599* (2013.01); *A61F 2002/30841* (2013.01); *A61F 2002/30891* (2013.01); *A61F 2002/30906* (2013.01); *A61F 2002/30909* (2013.01); *A61F 2002/30914* (2013.01); *A61F 2002/30943* (2013.01); *A61F 2002/30945* (2013.01); *A61F 2002/30952* (2013.01); *A61F 2002/30953* (2013.01); *A61F 2002/30957* (2013.01); *A61F 2002/30958* (2013.01); *A61F 2002/30962* (2013.01); *A61F 2002/30968* (2013.01); *A61F 2002/30985* (2013.01); *A61F 2002/4475* (2013.01); *A61F 2310/00017* (2013.01); *A61F 2310/00023* (2013.01); *A61F 2310/00029* (2013.01); *A61F 2310/00047* (2013.01); *A61F 2310/0097* (2013.01); *A61F 2310/00179* (2013.01); *A61F 2310/00598* (2013.01); *A61F 2310/00796* (2013.01); *A61F 2310/00958* (2013.01); *A61F 2310/00976* (2013.01)

(56) References Cited

U.S. PATENT DOCUMENTS

| | | |
|---|---|---|
| 4,686,970 A | 8/1987 | Dove et al. |
| 4,820,305 A | 4/1989 | Harms et al. |
| 4,904,261 A | 2/1990 | Dove et al. |
| 4,938,771 A | 7/1990 | Vecsei et al. |
| 5,030,233 A | 7/1991 | Ducheyne |
| 5,147,402 A | 9/1992 | Bohler et al. |
| 5,201,768 A | 4/1993 | Caspari et al. |
| 5,282,861 A | 2/1994 | Kaplan |
| 5,336,266 A | 8/1994 | Caspari et al. |
| 5,433,750 A | 7/1995 | Gradinger et al. |
| 5,571,185 A | 11/1996 | Schug |
| 5,609,635 A | 3/1997 | Michelson |
| 5,609,637 A | 3/1997 | Biedermann et al. |
| 5,676,700 A | 10/1997 | Black et al. |
| 5,702,449 A | 12/1997 | McKay |
| 5,702,451 A | 12/1997 | Biedermann et al. |
| 5,879,385 A | 3/1999 | Crockard et al. |
| 5,897,556 A | 4/1999 | Drewry et al. |
| 5,954,504 A * | 9/1999 | Misch ................ A61C 8/0018 433/173 |
| 5,989,290 A | 11/1999 | Biedermann et al. |
| 6,010,502 A | 1/2000 | Bagby |
| 6,143,032 A | 11/2000 | Schafer et al. |
| 6,149,689 A | 11/2000 | Grundei et al. |
| 6,206,924 B1 * | 3/2001 | Timm ................ A61F 2/28 623/17.11 |
| 6,245,110 B1 | 6/2001 | Grundei et al. |
| 6,264,695 B1 | 7/2001 | Stoy |
| 6,280,478 B1 | 8/2001 | Richter et al. |
| 6,290,726 B1 | 9/2001 | Pope et al. |
| 6,379,385 B1 | 4/2002 | Kalas et al. |
| 6,464,727 B1 | 10/2002 | Sharkey et al. |
| 6,585,770 B1 | 7/2003 | White et al. |
| 6,660,041 B1 | 12/2003 | Grundei |
| 6,712,852 B1 | 3/2004 | Chung et al. |
| D493,533 S | 7/2004 | Blain |
| 6,761,738 B1 | 7/2004 | Boyd |
| 6,866,682 B1 | 3/2005 | An et al. |
| 6,881,228 B2 | 4/2005 | Zdeblick et al. |
| 6,931,812 B1 | 8/2005 | Lipscomb |
| 6,972,019 B2 | 12/2005 | Michelson |
| 7,156,874 B2 | 1/2007 | Paponneau et al. |
| 7,163,560 B2 | 1/2007 | Mason |
| 7,163,561 B2 | 1/2007 | Michelson |
| 7,208,222 B2 | 4/2007 | Rolfe et al. |
| 7,291,149 B1 | 11/2007 | Michelson |
| 7,572,293 B2 | 8/2009 | Rhodes et al. |
| 7,578,850 B2 | 8/2009 | Kuczynski et al. |
| 8,292,967 B2 | 10/2012 | Brown et al. |
| 8,998,990 B2 | 4/2015 | Bertagnoli et al. |
| 9,271,845 B2 * | 3/2016 | Hunt .................... A61F 2/30 |
| 2004/0082999 A1 | 4/2004 | Mathys et al. |
| 2004/0121451 A1 | 6/2004 | Mortiz et al. |
| 2004/0236336 A1 | 11/2004 | Foerster |
| 2005/0015154 A1 | 1/2005 | Lindsey et al. |
| 2005/0033425 A1 | 2/2005 | Schwab |
| 2005/0129726 A1 | 6/2005 | Liebschner |
| 2005/0143827 A1 * | 6/2005 | Globerman ........ A61B 17/1637 623/17.16 |
| 2005/0171613 A1 | 8/2005 | Sartorius et al. |
| 2005/0222683 A1 | 10/2005 | Berry |
| 2006/0106461 A1 | 5/2006 | Embry et al. |
| 2006/0147332 A1 | 7/2006 | Jones et al. |
| 2006/0200062 A1 | 9/2006 | Saadat |
| 2007/0027544 A1 | 2/2007 | McCord et al. |
| 2007/0032876 A1 | 2/2007 | Clark |
| 2007/0055376 A1 | 3/2007 | Michelson |
| 2007/0179610 A1 | 8/2007 | Biedermann et al. |
| 2007/0233248 A1 | 10/2007 | Schwab et al. |
| 2007/0255420 A1 | 11/2007 | Johnson et al. |
| 2007/0270956 A1 | 11/2007 | Heinz |
| 2008/0014457 A1 | 1/2008 | Gennaro et al. |
| 2008/0071356 A1 | 3/2008 | Greenhalgh et al. |
| 2008/0154314 A1 | 6/2008 | McDevitt |
| 2009/0228112 A1 | 9/2009 | Clark et al. |
| 2010/0106194 A1 | 4/2010 | Bonutti |
| 2010/0161061 A1 | 6/2010 | Hunt |
| 2010/0174377 A1 | 7/2010 | Heuer |
| 2010/0174380 A1 | 7/2010 | Lewis |
| 2010/0179667 A1 | 7/2010 | Day et al. |
| 2010/0228355 A1 | 9/2010 | Linares |
| 2010/0298950 A1 | 11/2010 | McDonnell et al. |
| 2011/0022180 A1 | 1/2011 | Melkent et al. |
| 2011/0196495 A1 | 8/2011 | Hunt |
| 2011/0251690 A1 | 10/2011 | Berger |
| 2011/0313532 A1 | 12/2011 | Hunt |
| 2013/0030529 A1 | 1/2013 | Hunt |
| 2013/0123935 A1 | 5/2013 | Hunt |
| 2013/0158672 A1 | 6/2013 | Hunt |
| 2013/0218282 A1 | 8/2013 | Hunt |
| 2014/0121776 A1 | 5/2014 | Hunt |
| 2014/0288649 A1 | 9/2014 | Hunt |
| 2014/0288650 A1 | 9/2014 | Hunt |
| 2015/0282933 A1 | 10/2015 | Hunt |
| 2015/0282945 A1 | 10/2015 | Hunt |
| 2015/0282946 A1 | 10/2015 | Hunt |

FOREIGN PATENT DOCUMENTS

| | | |
|---|---|---|
| DE | 19721661 | 11/1998 |
| DE | 102006047663 | 4/2008 |
| EP | 0268115 | 1/1991 |
| EP | 0489684 | 6/1992 |
| WO | 0128460 | 4/2001 |
| WO | 2008022206 | 2/2008 |
| WO | 2010080511 | 7/2010 |

(56) References Cited

FOREIGN PATENT DOCUMENTS

OTHER PUBLICATIONS

"Midlantic Medical Systems—Geo Structure Rectangles (Posterior Approach)" accessed Jun. 11, 2008 at <http://www.midlanticmedical.com/products/anteriorColumnSpacers.php?p=2>. (p. 1).
"Midlantic Medical Systems—Nexus (Transverse Approach)" accessed Jun. 11, 2008 at <http://www.midlanticmedical.com/products/anteriorColumnSpacers.php?p=4>. (p. 1).
"Zimmer® Trabecular Metal™ Technology", accessed at <http://www.zimmerindia.com/z/ctl/op/global/action/1/id/9512/template/PC/navid/8173>, Jul. 9, 2006. (pp. 1-5).
"Multifunctional Electrochemical Energy Storage Materials", accessed on Oct. 1, 2008 at <http://www.uvapf.org/technologies/index.cfm/fuseaction/invention/invention_id/85/?CFID=1785971&CFTOKEN=59649784&>. (pp. 1-2).
"Image: C60a.phg", Wikipedia, accessed on Oct. 1, 2008 at <http://en.wikipedia.org/wiki/Image:C60a.png>. pp. 1-3).
"Image:POV-Ray-Dodecahedron.svg", Wikipedia, accessed at on Oct. 1, 2008 at <http://en.wikipedia.org/wiki/Image:POV-Ray-Dodecahedron.svg>. (pp. 1-4).
"Image:Icosahedron.svg", Wikipedia, accessed on Oct. 1, 2008 at <http://en.wikipedia.org/wiki/Image:Icosahedron.svg>. (pp. 1-2).
"Image:Octahedron.svg", Wikipedia, accessed on Oct. 1, 2008 at <http://en.wikipedia.org/wiki/Image:Octahedron.svg>. (pp. 1-3).
"Truss" Wikipedia, accessed at <http://en.wikipedia.org/wiki/Truss>, Dec. 16, 2009. (pp. 1-9).
"NexGen Trabecular Metal Tibial Cone Augments" accessed at <http://catalog.zimmer.com/content/zpc/products/200/250/C60/CE008/2653.html>, Nov. 17, 2009. (p. 1).
"Spinal Kinetics", accessed on Oct. 6, 2009 at <http://www.spinalkinetics.com/m6systems.html>. (p. 1).
"CINN", accessed on Oct. 6, 2009 at <http://www.cinn.org/cr-articles/CR-artificial-disc.html>, Copyright 2008. (pp. 1-9).
"Zimmer Anatomical Shoulder Fracture System", copyright 2007. (pp. 1-6).
"Wolff's Law", Wikipedia, accessed at <http://en.wikipedia.org/wiki/Wolff's_law>, Jun. 9, 2010. (pp. 1-2).
"e-Manufacturing is making its inroad to series production", Nov. 20, 2008. (pp. 1-2).
"InFix Anterior Lumbar Device" Dec. 17, 2009. (p. 1).
"Biofoam Wedge System" Wright, Copyright 2010. (pp. 1-4).
"LPT2 Great Toe Implant" Wright, Copyright 2008. (p. 1-16).
"Biofoam Wedge System Surgical Technique" Wright, Copyright 2010. (pp. 1-12).
Murr et al. "Next-generation biomedical implants using additive manufacturing of complex, cellular and functional mesh arrays", Philosophical Transactions of the Royal Society, Mar. 22, 2010, vol. 368, No. 1917, pp. 1999-2032.
Yan, et al. "Mechanical strain regulates osteoblast proliferation through integrin-mediated ERK activation", PloS One, Apr. 23, 2012, vol. 7, No. 4, Article No. e35709.
Distension Blog located at htpp://kineticdistensio.blogspot.com/2011_10_0_archive.html including entry of Oct. 14, 2011.
Baranovskaya et al. ITECH M. Sc. Programme-Uni Stuttgart, Institut Fur Computerbasiertes Entwerfen (ICD, Stuttgart, Germany located at htpp://architecture-is-yes.tumblr.com/post/8525760 accessed Aug. 21, 2015.
Office Action for U.S. Appl. No. 12/640,825 issued Aug. 30, 2012.
EPO International Search Report and Written Opinion for PCT/US2009/068512 mailed May 12, 2010. (pp. 1-61).
International Preliminary Report on Patentability for PCT/US2009/068512 dated Mar. 31, 2011. (pp. 1-8).
Office Action for U.S. Appl. No. 12/960,092 issued Aug. 20, 2014.
Office Action for U.S. Appl. No. 12/960,092 issued Apr. 24, 2015.
Australian Examination Report for Australian Patent Application No. 2009335771 dated Jan. 14, 2014.
Canadian Examination Report for Canadian Patent Application No. 2,746,505 dated Dec. 1, 2015.
European Examination Report for EP Application No. 09796208.8 dated Feb. 7, 2014.
European Examination Report for EP Application No. 09796208.8 dated Aug. 21, 2014.
Office Action for U.S. Appl. No. 14/743,579 issued Apr. 5, 2016.
Office Action for U.S. Appl. No. 14/743,607 issued Apr. 6, 2016.
Office Action for U.S. Appl. No. 12/818,508 issued Feb. 4, 2013.
Final Office Action for U.S. Appl. No. 12/818,508 issued Aug. 15, 2013.
Office Action for U.S. Appl. No. 12/818,508 issued May 22, 2015.
Final Office Action for U.S. Appl. No. 12/818,508 issued Nov. 20, 2015.
EPO International Search Report and Written Opinion for PCT/US2011/040117 mailed Aug. 12, 2011.
International Preliminary Report on Patentability for PCT/US2011/040117 dated Dec. 19, 2012.
Office Action for U.S. Appl. No. 13/805,231 issued Aug. 20, 2015.
Final Office Action for U.S. Appl. No. 13/805,231 issued Dec. 11, 2015.
Australian Examination Report for AU Application No. 2011267941 dated Jan. 16, 2014.
Japanese Examination Report for JP Application No. 2013-515407 dated Feb. 24, 2015.
Japanese Examination Report for JP Application No. 2013-515407 dated Nov. 24, 2015.
Office Action for U.S. Appl. No. 13/194,561 issued Mar. 19, 2013.
Final Office Action for U.S. Appl. No. 13/194,561 issued Sep. 26, 2013.
Office Action for U.S. Appl. No. 13/194,561 issued Jan. 20, 2015.
International Search Report and Written Opinion for PCT/US2012/048300 May 7, 2013.
International Preliminary Report on Patentability for PCT/US2012/048300 Feb. 4, 2014.
Japanese Examination Report for JP Application No. 2014-523976 dated May 24, 2016.
International Search Report and Written Opinion for PCT/US2012/045717 issued Jan. 30, 2013.
International Preliminary Report on Patentability for PCT/US2012/045717 dated Jan. 7, 2014.
Office Action for U.S. Appl. No. 13/668,968 issued Aug. 18, 2014.
Office Action for U.S. Appl. No. 13/668,968 issued Jan. 7, 2015.
Office Action for U.S. Appl. No. 13/668,968 issued Jun. 29, 2015.
Office Action for U.S. Appl. No. 13/668,968 issued Apr. 14, 2016.
International Search Report and Written Opinion for PCT/US2012/063600 issued Jan. 31, 2013.
International Preliminary Report on Patentability for PCT/US2012/063600 issued May 6, 2014.
Supplemental European Search Report for EP Application No. 12846553.1 issued May 20, 2015.
Office Action for U.S. Appl. No. 13/762,825 issued Jul. 2, 2014.
Office Action for U.S. Appl. No. 13/762,825 issued Dec. 12, 2014.
Office Action for U.S. Appl. No. 13/762,825 issued Mar. 7, 2016.
International Search Report and Written Opinion for PCT/US2013/025281 issued May 15, 2013.
International Preliminary Report on Patentability for PCT/US2013/025281 issued Aug. 12, 2014.
Office Action for U.S. Appl. No. 14/036,974 issued Jul. 22, 2015.
International Search Report and Written Opinion for PCT/US2013/061725 issued Jan. 13, 2014.
International Preliminary Report on Patentability for PCT/US2013/061725 issued Mar. 13, 2015.
Chinese Examination Report for CN Application No. 20130055597.3 dated Apr. 5, 2016.
International Search Report and Written Opinion for PCT/US2014/030319 issued Apr. 6, 2015.
Office Action for U.S. Appl. No. 14/216,087 issued Aug. 27, 2015.
International Search Report and Written Opinion for PCTUS201430358 issued Aug. 27, 2014.

* cited by examiner

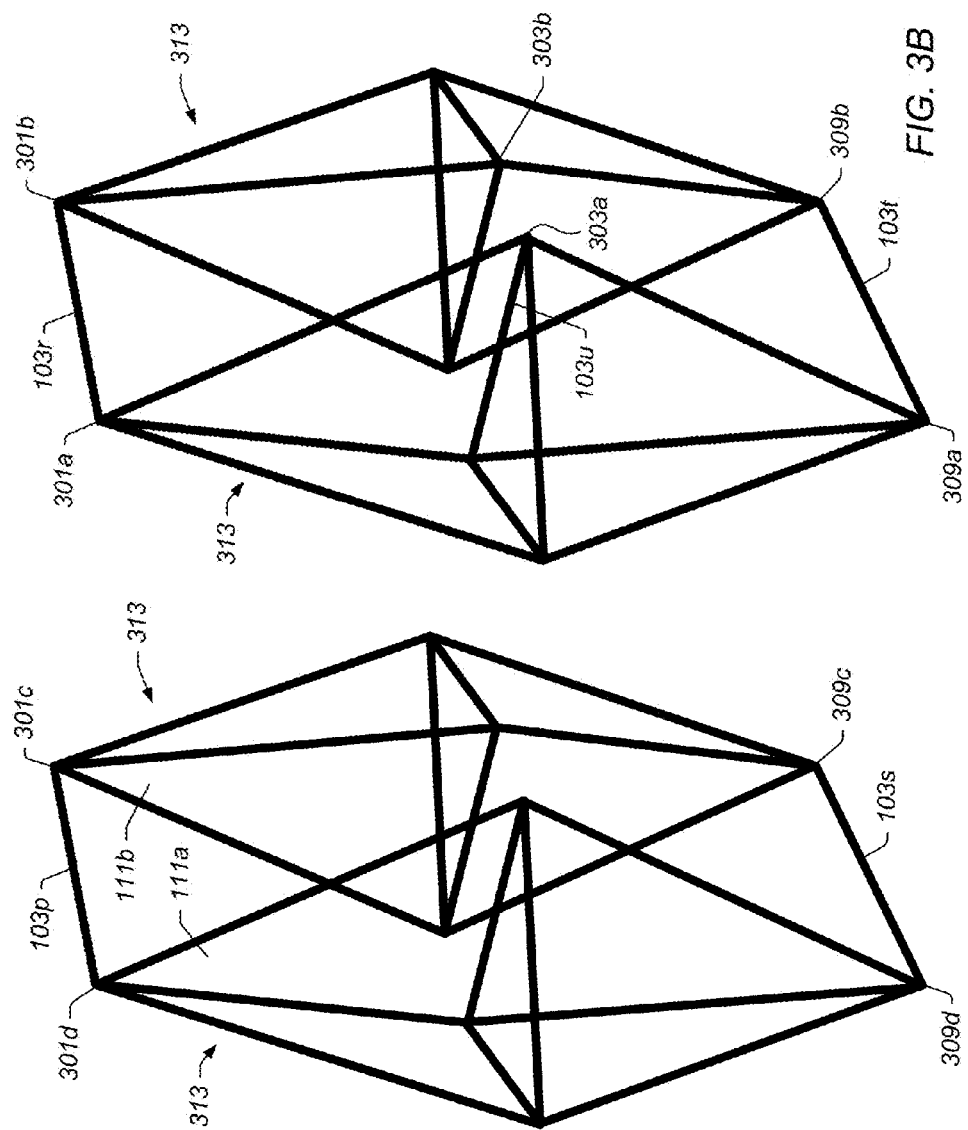

SPINAL PROGRAMMABLE IMPLANT

PRIORITY CLAIM

This application is a continuation application of U.S. patent application Ser. No. 14/036,974 filed on Sep. 25, 2013 which claims the benefit of U.S. Provisional Application No. 61/705,403 filed on Sep. 25, 2012 and U.S. Provisional Application No. 61/801,597 filed on Mar. 15, 2013.

BACKGROUND OF THE INVENTION

1. Field of the Invention

The present invention relates generally to medical devices and, more specifically, to implants.

2. Description of the Relevant Art

Implants may be used in human and/or animals to support and/or secure one or more bones. For example, implants may be used in the spine to support and/or replace damaged tissue between the vertebrae in the spine. Once implanted between two vertebrae, the implant may provide support between the two vertebrae and bone growth may take place around and through the implant to at least partially fuse the two vertebrae for long-term support. Implants may include relatively large rims with solid material that may cover, for example, 50% of the area that interacts with the endplate. The rim may provide a contact area between the implant and the vertebral endplates. Large rims may have several drawbacks. For example, large rims may impede bone growth and reduce the size of the bone column fusing the superior and inferior vertebral bodies. Additionally, large rims preferentially support and regionalize loads, preventing distribution of force and accommodating response. The process of localizing loading also serves to under load other areas of the vertebral bodies, thereby activating regional resorption according to negative microstrain.

Spinal implants may include open channels through the center of the supporting rims in a superior/inferior direction. The open channel design may require members of the implant that separate the rims that interact with the vertebral endplates to absorb the compressive forces between the vertebral endplates. This may increase the pressure on smaller areas of the vertebral endplates and may potentially lead to stress risers in the vertebral endplates. Further, while bone graft material is often used in conjunction with implants to encourage bone growth, the open column design of implants may reduce the likelihood of bone graft material from securing itself to the implant which could result in a bio-mechanical cooperation that is not conducive to promoting good fusion.

Bone graft material may be packed into the implant in a high-pressure state to prevent bone graft material from exiting the implant while being placed between the vertebral endplates. The high-pressure state may also reduce the potential for the bone graft material loosening due to motion between the implant and the vertebral endplates or compressive forces experienced during settling of the implant. In addition, a high-pressure environment may allow the bone graft material to re-model and fuse at greater strength. High-pressure states, however, may be difficult to create and maintain for the bone graft material in an implant. In particular, the lack of attachment of the bulk graft cannot fully accept or integrate the differential loading anticipated in normal kinetic scope.

Various embodiments of implant systems and related apparatus, and methods of operating the same are described herein. In various embodiments, an implant for interfacing with a bone structure includes a web structure, including a space truss, configured to interface with human bone tissue, including cells, matrix, and ionic milieu. The space truss includes two or more planar truss units having a plurality of struts joined at nodes.

In an embodiment, an implant for interfacing with a bone structure includes: a web structure that is formed from a plurality of struts joined at nodes, wherein the web structure is configured to interface with human bone tissue. The diameter and/or length of the struts and/or the density of the web structure are predetermined such that when the web structure is in contact with the bone structure, its matrix, or the cells from which it is derived, at least a portion of the struts create a microstrain, that is transferred to the adherent osteoblasts, bone matrix, or lamellar tissue, of between about $1\mu\epsilon$ and about $5000\mu\epsilon$, or between about $500\mu\epsilon$ and $2000\mu\epsilon$, or between about $1000\mu\epsilon$ and about $1500\mu\epsilon$ or to a negative reflection of compression in interval and resonance with loading in both flexion, extension, torque, or combinations thereof. These ranges are optimized to known load-response dynamics, but are meant as guides rather than limitations to the activity and response. The diameter and/or length of the struts is predetermined so that at least a portion of the struts during loading create a change in length of the adherent osteoblasts, bone matrix, or lamellar tissue, of between about 0.05% and about 0.2% or between about 0.1% and about 0.15% causing an osteogenic response. Struts may have a length of between about 1 mm to about 100 mm. The diameter of the strut may be predetermined such that the struts create a change in length of the adhered osteoblasts of between about 0.05% and 0.2% when the web structure is in contact with the bone structure. Alternatively, the diameter of the strut is predetermined such that the strut undergoes a change of length of between about 0.000125% and 0.0005%, or between about 0.00025% and 0.000375%. In some embodiments, at least a portion of the struts are composed of struts having a length of 1 mm to 100 mm and a diameter ranging between 0.250 mm and 5 mm.

In an embodiment, an implant for interfacing with a bone structure includes a web structure that is formed from a plurality of struts joined at nodes, wherein the web structure is configured to interface with human bone tissue. The web structure, in some embodiments, includes a first bone contact surface and a second bone contact surface. A first portion of struts that comprise the space truss have a physical property that is different from a second portion of the struts that comprise the space truss. The first portion of struts that comprise the space truss may have: a deformation strength; a defined length; a diameter; a differential diameter along its length; a density; a porosity; or any combination of these physical properties; that is different from the second portion of the struts that comprise the space truss. In an embodiment, the space truss includes one or more central struts extending from the first bone contact surface to the second bone contact surface, wherein the central struts have a deformation strength that is greater than or less than the surrounding struts. In an embodiment, the space truss comprises one or more longitudinal struts extending parallel to the first bone contact surface and/or the second bone contact surface, wherein the longitudinal struts have a deformation strength that is greater than or less than the surrounding struts. The diameter of the first portion of the struts may be greater than a diameter of the second portion of the struts. The material used to form the first portion of struts may be different from the material used to form the second portion of struts.

BRIEF DESCRIPTION OF THE DRAWINGS

Advantages of the present invention will become apparent to those skilled in the art with the benefit of the following detailed description of embodiments and upon reference to the accompanying drawings in which:

FIGS. 3A-3B illustrate a web structure formed with triangular-shaped building blocks, according to an embodiment.

Figure 1A:
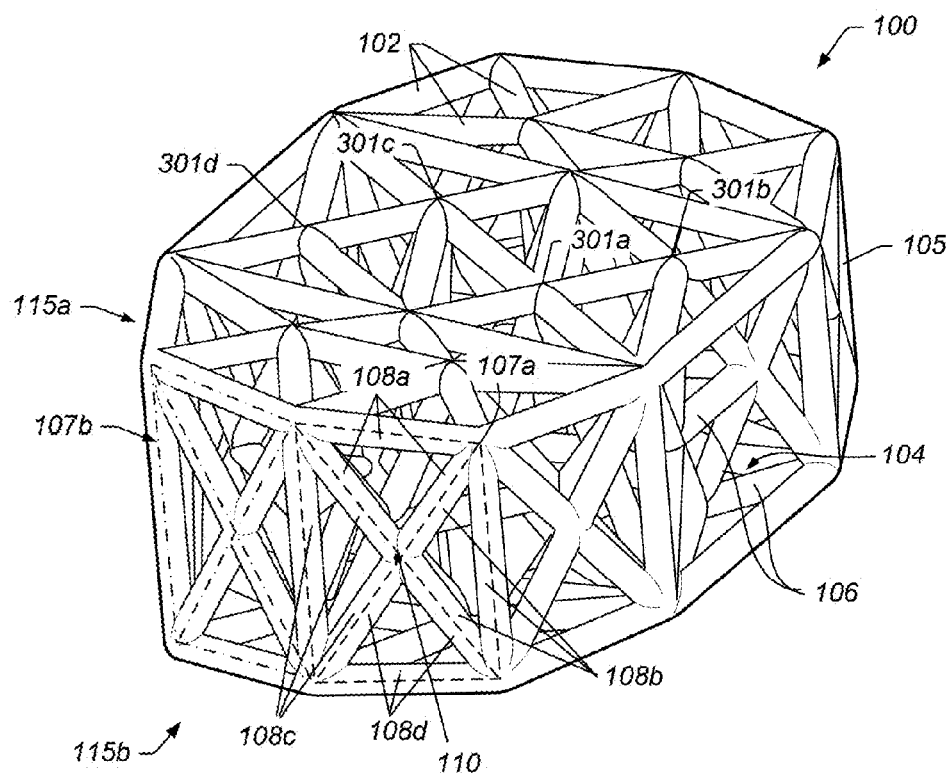
FIGS. 1A-1B illustrate views of an implant with lordosis, according to an embodiment.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents, and alternatives falling within the spirit and scope of the present invention as defined by the appended claims. Note, the headings are for organizational purposes only and are not meant to be used to limit or interpret the description or claims.

DETAILED DESCRIPTION OF THE PREFERRED EMBODIMENTS

Figure 1B:
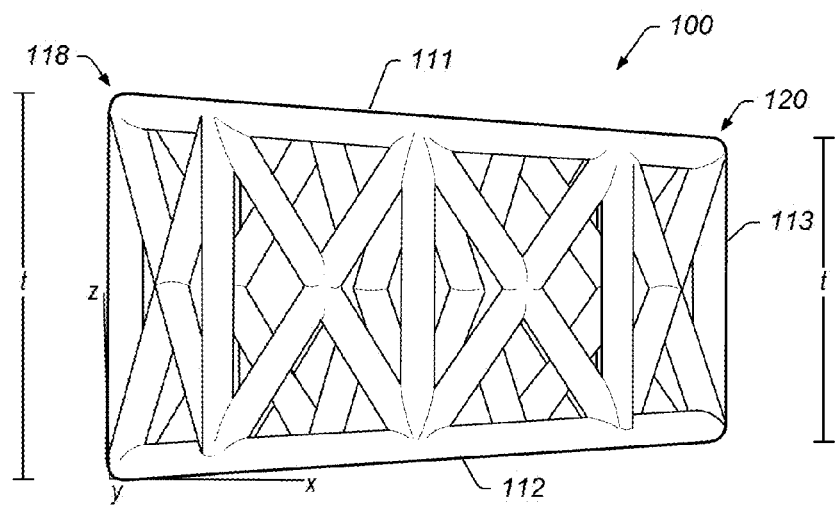

FIGS. 1A-1B illustrate views of implant 100, according to an embodiment. The specifically depicted implant 100 may be used, for example, in anterior lumbar inter-body fusion (ALIF) or posterior lumbar inter-body fusion (PLIF), however, it should be understood that implant 100 nay have a variety of shapes suitable for bone fusion applications. In some embodiments, implant 100 may include a web structure with one or more trusses 102 (e.g., planar and space trusses). Implant 100 may be used in various types of implants for humans or animals such as spinal implants, corpectomy devices, knee replacements, hip replacements, long bone reconstruction scaffolding, and cranio-maxifacial implants foot and ankle, hand and wrist, shoulder and elbow (large joint, small joint, extremity as well as custom trauma implants). Other implant uses are also contemplated.

As used herein a "truss structure" is a structure having one or more elongate struts connected at joints referred to as nodes. Trusses may include variants of a pratt truss, king post truss, queen post truss, town's lattice truss, planar truss, space truss, and/or a vierendeel truss (other trusses may also be used). A "truss unit" is a structure having a perimeter defined by three or more elongate struts."

As used herein a "planar truss" is a truss structure where all of the struts and nodes lie substantially within a single two-dimensional plane. A planar truss, for example, may include one or more "truss units" where each of the struts is a substantially straight member such that the entirety of the struts and the nodes of the one or more truss units lie in substantially the same plane. A truss unit where each of the struts is a substantially straight strut and the entirety of the struts and the nodes of the truss unit lie in substantially the same plane is referred to as a "planar truss unit."

As used herein a "space truss" is a truss having struts and nodes that are not substantially confined in a single two-dimensional plane. A space truss may include two or more planar trusses (e.g., planar truss units) wherein at least one of the two or more planar trusses lies in a plane that is not substantially parallel to a plane of at least one or more of the other two or more planar trusses. A space truss, for example, may include two planar truss units adjacent to one another (e.g., sharing a common strut) wherein each of the planar truss units lie in separate planes that are angled with respect to one another (e.g., not parallel to one another).

As used herein a "triangular truss" is a structure having one or more triangular units that are formed by three straight struts connected at joints referred to as nodes. For example, a triangular truss may include three straight elongate strut members that are coupled to one another at three nodes to from a triangular shaped truss. As used herein a "planar triangular truss" is a triangular truss structure where all of the struts and nodes lie substantially within a single two-dimensional plane. Each triangular unit may be referred to as a "triangular truss unit." A triangular truss unit where each of the struts is a substantially straight member such that the entirety of the struts and the nodes of the triangular truss units lie in substantially the same plane is referred to as a "planar triangular truss unit." As used herein a "triangular space truss" is a space truss including one or more triangular truss units.

In various embodiments, the trusses 102 of the web structure may include one or more planar truss units (e.g., planar triangular truss units) constructed with straight or curved/arched members (e.g., struts) connected at various nodes. In some embodiments, the trusses 102 may be micro-trusses. A "micro-truss" is a truss having dimensions sufficiently small enough such that a plurality of micro-trusses can be assembled or otherwise coupled to one another to form a web structure having a small enough overall dimension (e.g., height, length and width) such that substantially all of the web structure can be inserted into an implant location (e.g., between two vertebra). Such a web structure and its micro-trusses can thus be employed to receive and distribute throughout the web structure loading forces of the surrounding tissue (e.g., vertebra, bone, or the like). In one embodiment, the diameters of the struts forming the micro-truss may be between about 0.25 millimeters (mm) and 5 mm in diameter (e.g., a diameter of about 0.25 mm, 0.5 mm, 0.6 mm, 0.7 mm, 0.8 mm, 0.9 mm, 1 mm, 2 mm, 3 mm, 4 mm, or 5 mm). In one embodiment, a micro-truss may have an overall length or width of less than about 1 inch (e.g., a length less than about 0.9 in, 0.8 in, 0.7 in, 0.6 in, 0.5 in, 0.4 in, 0.3 in, 0.2 in, 0.1 in).

As depicted, for example, in FIGS. 1A-1B, the web structure may extend throughout implant 100 (including the central portion of implant 100) to provide support throughout implant 100. Trusses 102 of implant 100 may thus support implant 100 against tensile, compressive, and shear forces. Web structure may also reinforce implant 100 along multiple planes. The external truss structure may, for example, provide support against tensile and compressive forces acting vertically through the implant, and the internal web structure may provide support against tensile, compressive, and shear forces along the various planes containing the respective trusses. In some embodiments, the web structure includes trusses 102 that form a triangulated web structure with multiple struts (e.g., struts 103a-f) (struts are generally referred to herein as "struts 103").

In one embodiment, web structure of the implant 100 may include an internal web structure that is at least partially enclosed by an external truss structure. For example, in one embodiment, web structure 101 may include an internal web structure that includes a space truss having at least a portion of the space truss surrounded by an external truss structure that includes one or more planar trusses formed with a plurality of planar truss units that lie substantially in a single plane. FIG. 1A depicts an embodiment of implant 100 having an internal web structure 104 and an external truss structure 105. In the illustrated embodiment, internal web structure 104 includes a space truss defined by a plurality of planar truss units 106 coupled at an angle with respect to one another such that each adjacent truss unit is not co-planar with each adjacent truss units. Adjacent truss units may include two truss units that share a strut and the respective two nodes at the ends of the shared strut.

In one embodiment, external truss structure 105 includes a plurality of planar trusses that are coupled about an exterior, interior or other portion of the implant. For example, in the illustrated embodiment, the external truss structure 105 includes a series of planar trusses 107a,b that are coupled to one another. Planar truss 107a is denoted by a dashed line [- - - - -], planar truss 107b is denoted by dotted-dashed line [- • - • -]. Each planar truss is formed from a plurality of planar truss units (e.g., triangular planar truss units. As depicted, planar truss 107a includes four triangular planar truss units 108a,b,c,d having a common vertex 110 and arranged to form a generally rectangular structure that lies in a single common plane. In other words, the four triangular planar truss units are arranged to form a substantially rectangular structure having "X" shaped struts extend from one corner of the rectangular structure to the opposite corner of the rectangular structure. As depicted, the substantially rectangular structure may include a trapezoidal shape. As described in more detail below, the trapezoidal shape may be conducive to providing an implant including lordosis. Lordosis may include an angled orientation of surfaces (e.g., top and bottom) of an implant that provides for differences in thickness in anterior and posterior regions of the implant such that the implant is conducive for supporting the curvature of a vertebral column.

In one embodiment, the planar trusses that form the external truss are coupled to one another, and are aligned along at least one axis. For example, in FIG. 1A, planar truss section 107a is coupled to an adjacent planar truss 107b. Planer truss sections 107a,b are not parallel in all directions. Planar truss sections 107a,b are, however, arranged parallel to one another in at least one direction (e.g., the vertical direction between the top and the bottom faces of implant 100). For example, planar trusses 107a,b and the additional planar trusses are arranged in series with an angle relative to one another to form a generally circular or polygon shaped enclosure having substantially vertical walls defined by the planar trusses and the planar truss units arranged in the vertical direction.

Figure 2A:
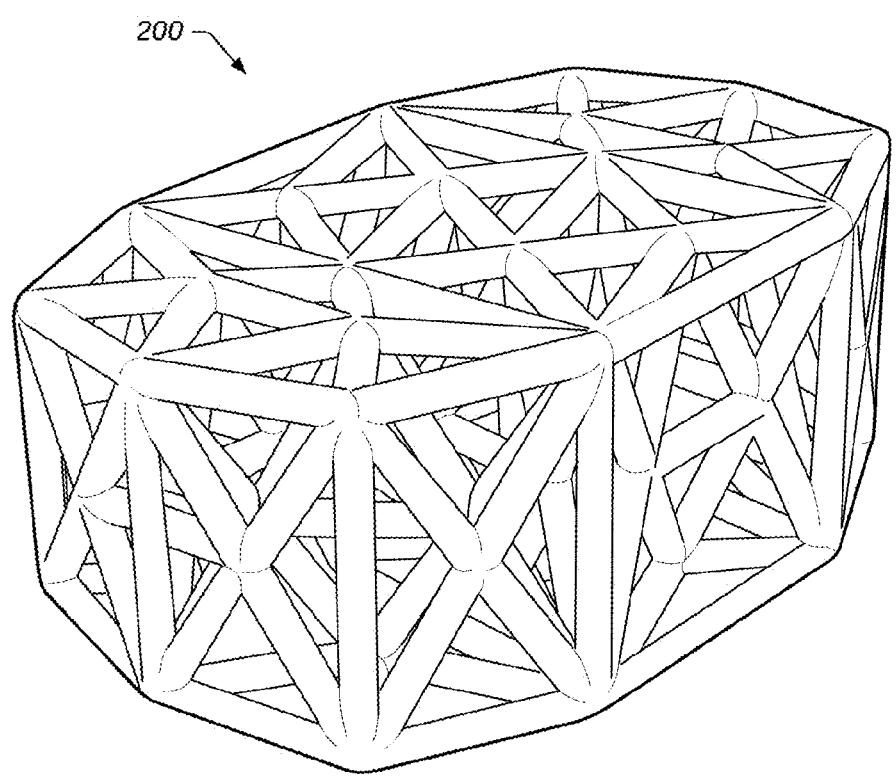
FIGS. 2A-2D illustrate views of an implant without lordosis, according to an embodiment.
Figure 2B:
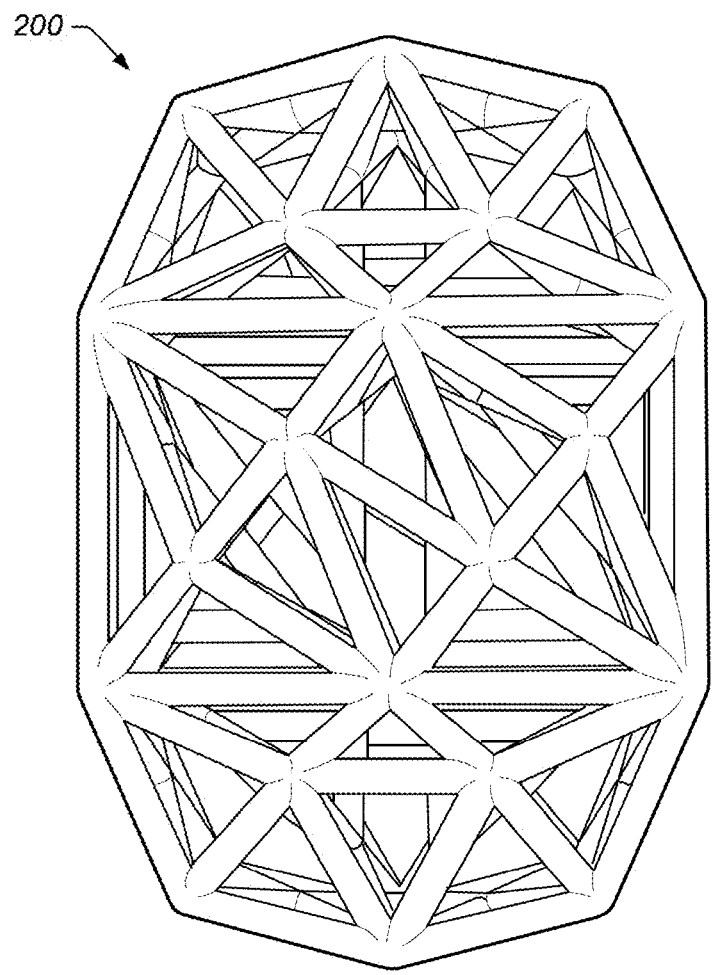
Figure 2C:
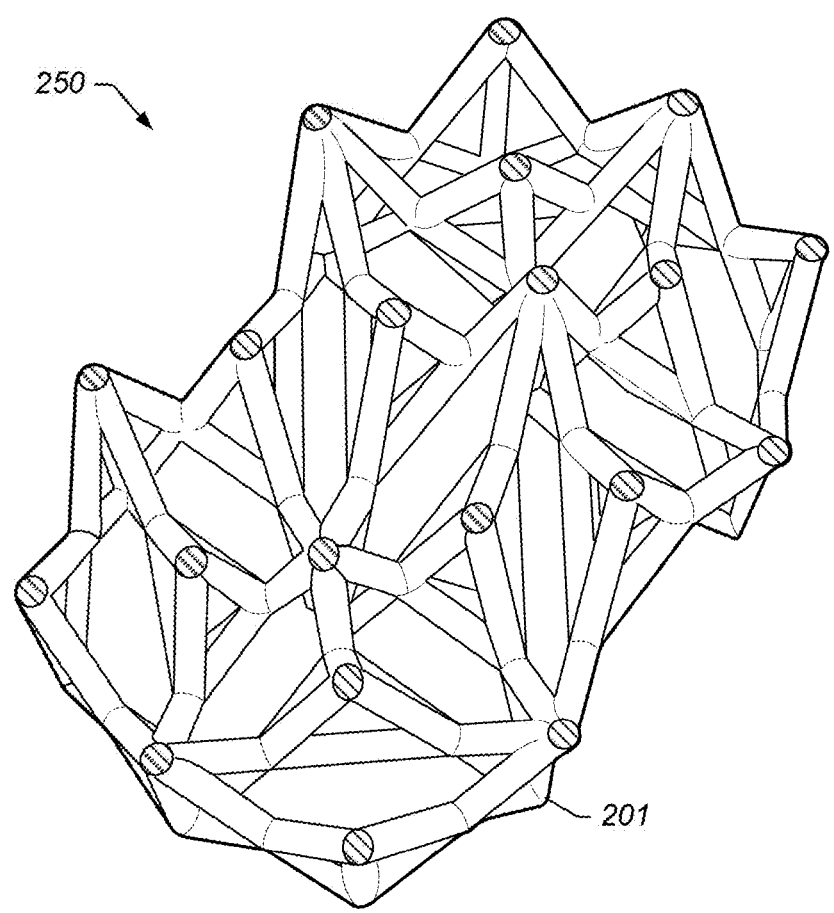

In one embodiment, the external truss portion may encompass the sides, top, and/or bottom of the implant. For example, in one embodiment, the external truss portion may include a top region, side regions, and/or a bottom region. FIG. 1A depicts an embodiment of implant 100 wherein external truss portion 105 includes a top 111, bottom 112 and a side region 113. As described above, side region 113 includes a series of planar trusses arranged vertically to form a circular/polygon ring-like structure that completely or at least partially surrounds the perimeter of the space truss disposed in the central portion of implant 100. In the depicted embodiment, top portion 111 of external truss structure 105 includes a plurality of truss units coupled to one another to form a planar truss that cover substantially all of the top region of internal web structure 104. In the illustrated embodiment, the top portion 111 spans entirely the region between top edges of the side portion 113 of external truss structure 105. In the illustrated embodiment, top portion 111 is formed from a single planar truss that includes a plurality of truss units that lie in substantially the same plane. In other words, the planar truss of top portion 111 defines a generally flat surface. Although difficult to view in FIG. 1, the underside of implant 100 may include the bottom portion 112 having a configuration similar to that of the top portion 111. In other embodiments, external truss structure 105 may include a partial side, top and/or bottom external truss portions. Or may not include one or more of the side, top and bottom external truss portions. For example, as described in more detail below, FIG. 2C depicts an embodiment of implant 100 that includes an internal web structure formed from space trusses, that does not have an external truss structure.

In some embodiments, implant 100 may be formed from a biocompatible material such as a titanium alloy (e.g., γTitanium Aluminides), cobalt, chromium, stainless steel, Polyetheretherketone (PEEK), ceramics, etc. Other materials are also contemplated. In some embodiments, implant 100 may be made through a rapid prototyping process (e.g., electron beam melting (EBM) process) as further described below. Other processes are also possible (e.g., injection molding, casting, sintering, selective laser sintering (SLS), Direct Metal Laser Sintering (DMLS), etc). SLS may include laser-sintering of high-performance polymers such as that provided by EOS of North America, Inc., headquartered in Novi, Mich., U.S.A. High-performance polymers may include various forms of PEEK (e.g., HP3 having a tensile strength of up to about 95 mega Pascal (MPa) and a Young's modulus of up to about 4400 MPa and continuous operating temperature between about 180° C. (356° F.) and 260° C. (500° F.)). Other materials may include PA 12 and PA 11 provided by EOS of North America, Inc.

Figure 7:
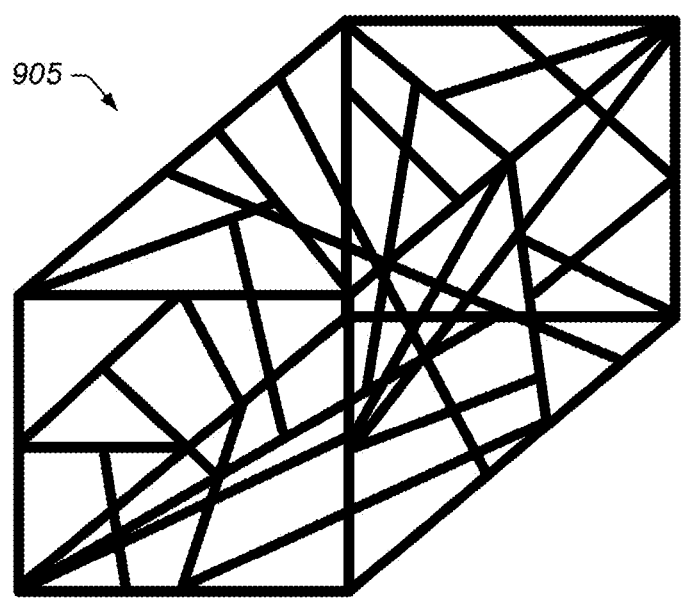
FIG. 7 illustrates a random web structure, according to an embodiment.

As described above, in some embodiments the web structure may be formed from a plurality of triangular planar truss units. In some embodiments, the planar truss units may be coupled to each other to define polyhedrons that define the internal web structure. Examples of polyhedron structures that may be created by joining planar truss units include, but are not limited to, tetrahedrons, pentahedrons, hexahedrons, heptahedrons, pyramids, octahedrons, dodecahedrons, icosahedrons, and spherical fullerenes. In some embodiments, such as those described above, the space truss of the web structure may connect multiple midpoints of tetrahedron building blocks and include a regular pattern of tetrahedron blocks arranged adjacent one another. In some embodiments, the web structure may not include a pattern of geometrical building blocks. For example, FIG. 7 illustrates an irregular pattern of struts that may be used in an implant 905. Other web structures are also contemplated. Examples of implants composed of a web structure are described in U.S. Published Patent Applications Nos.: 2010/0161061; 2011/0196495; 20110313532; and 2013/0030529, each of which is incorporated herein by reference.

Figure 3A:
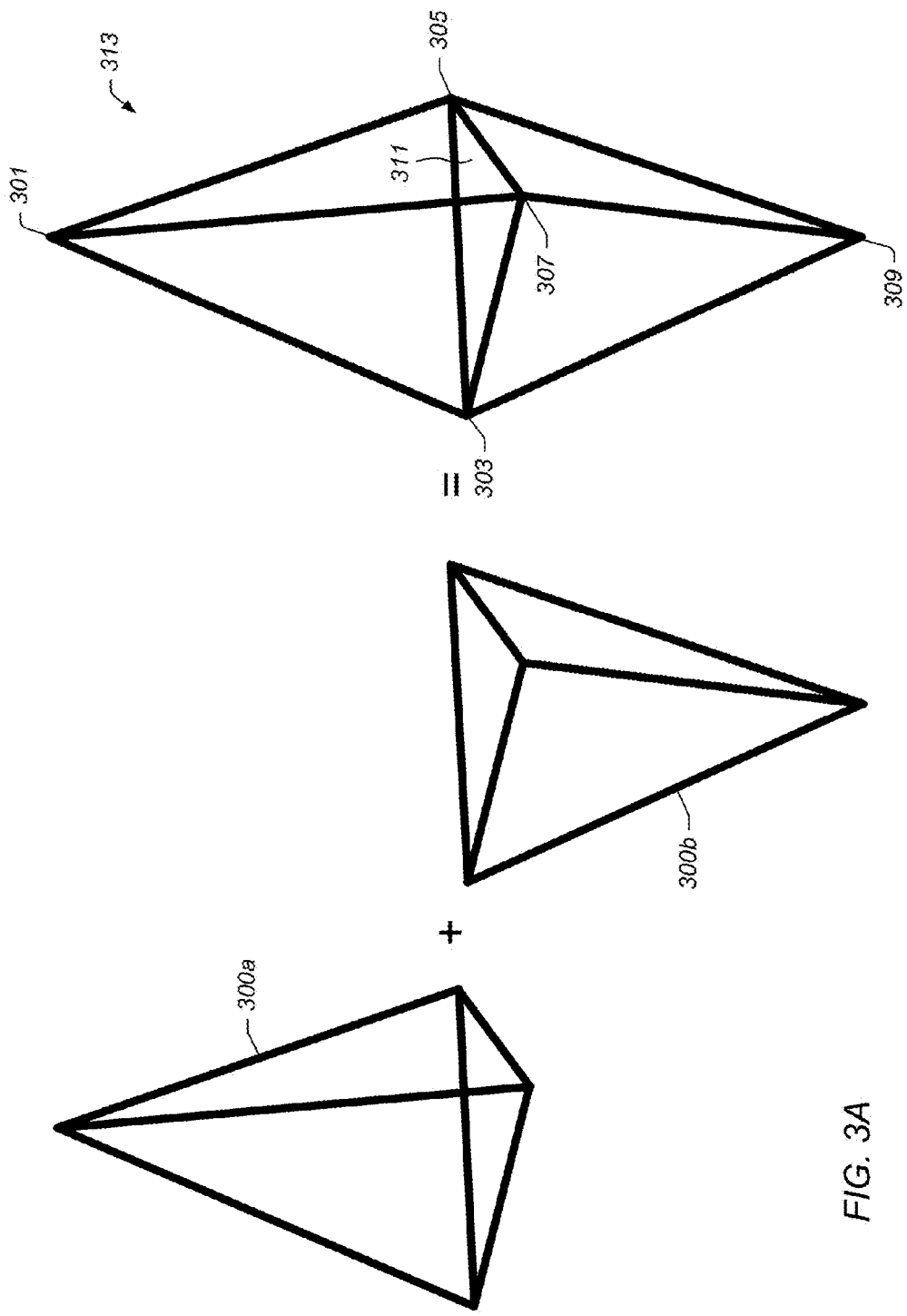

FIGS. 3A-3B illustrate a schematic view of a portion of an internal web structure formed with space units formed from triangular planar truss units. Triangular planar truss units may be joined together to form tetrahedrons 300a,b that may also be used as building blocks (other patterns from the triangles are also contemplated). Other building blocks are also contemplated (e.g., square-shaped building blocks). In some embodiments, a web structure may include a single tetrahedron, such as tetrahedron 300a or 300b alone or in combination with one or more other polyhedron. In some embodiments, a web structure may include two or more tetrahedrons 300a,b. Tetrahedron 300a may include four triangular faces in which three of the four triangles meet at each vertex. In some embodiments, two tetrahedrons 300a and 300b may be placed together at two adjacent faces to form space truss 313 with a hexahedron-shaped frame (including six faces). Hexahedron-shaped space truss 313 may include first vertex 301, second vertex 309, third vertex 303, fourth vertex 305, and fifth vertex 307. Common plane 311 may be shared by two tetrahedrons (e.g., common plane 311 may include third vertex 303, fourth vertex 305, and fifth vertex 307) to form a hexahedron with first vertex 301 and second vertex 309 spaced away from common plane 311. As depicted, the center portion of the triangular shaped building blocks may have a void region in their center that does not include any additional members (e.g., no members other than the struts forming the triangular shaped building blocks) extending there through.

As seen in FIG. 3B, in some embodiments, multiple hexahedron-shaped space trusses 313 may be arranged in a side-by-side manner. Two space trusses 313 of implant 100 may be connected via their first vertices 301a,b through strut 103r and connected via their second vertices 309a,b through strut 103t. Similarly, two space trusses 313 may be connected via their first vertices 301c,d through strut 103p and connected via their second vertices 309c,d through strut 103s. Other connections are also possible. For example, space trusses 313 may connect directly through side vertices (e.g., directly through corresponding vertices (such as vertices 303a,b) and/or share a common strut (such as strut 103u)) and/or through a side face (e.g., side faces 111a,b).

Figure 4A:
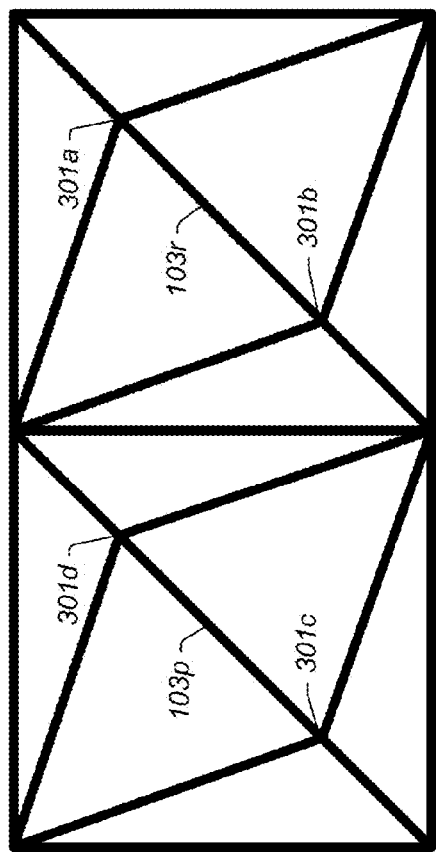
FIGS. 4A-4B illustrate a top structure of an internal web structure of the implant, according to an embodiment.
Figure 4B:
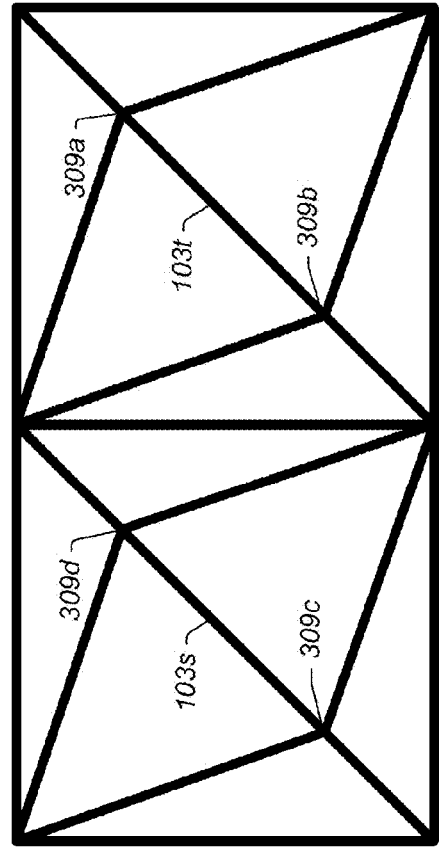

FIG. 4A illustrates additional struts 103 (e.g., struts 103p and 103r) connecting the first vertices (represented respectively by 301a, 301b, 301c, and 301d) of four hexahedron-shaped space trusses in implant 100. FIG. 4B illustrates additional struts 103 (e.g., struts 103s and 103t) connecting second vertices 309 (represented respectively by 309a, 309b, 309c, and 309d) of four hexahedron-shaped space trusses in implant 100. In some embodiments, additional struts 103 may also be used internally between one or more vertices of the web structures to form additional trusses (e.g., see web structures in FIGS. 1A-2B) (other structures are also possible).

As shown in FIG. 1A, top surface 115a and bottom surface 115b of implant 100 may include triangles, squares, circles or other shapes (e.g., a random or custom design). Top and bottom surfaces 115a,b may be used to connect the top and bottom vertices of various geometrical building blocks used in the web structure of implant 100. For example, each vertex may be connected through struts to the neighboring vertices of other geometrical building blocks. Top surface 115a may include other strut networks and/or connections. In some embodiments, bottom surface 115b may mirror the top surface (and/or have other designs). In some embodiments, top surface 115a and bottom surface 115b may engage respective surfaces of two adjacent vertebrae when implant 100 is implanted.

As depicted in FIG. 1B, implant 100 may include lordosis (e.g., an angle in top and/or bottom surfaces 115a,b approximately in a range of 4 to 15 degrees (such as 4, 5, 6, 7, 8, 9, 10, 11, 12, 13, 14, or 15 degrees)) to further support the adjacent vertebrae when implanted. As described above, lordosis may include an angled orientation of surfaces (e.g., top and bottom) that provide for differences in thickness in the anterior and posterior portions of the implant such that the implant is conducive for supporting the curvature of a vertebral column. In the illustrated embodiment, the thickness of implant 100 is greater at or near the anterior portion 118 and lesser at or near the posterior portion 120 of the implant. In the illustrated embodiment, the side portions of external truss structure are arranged substantially vertically, and the lordosis is formed by the angles of the top portion 111 and bottom portion 112 of external truss structure. For example, in the illustrated embodiment, top portion 111 and bottom portion 112 of external truss structure are not perpendicular to the vertical plane defined by the side portion 113. Rather, the top portion 111 and bottom portion 112 are arranged with an acute angle relative to the vertical plane of side portion 113 at or near the anterior region 118 of implant 100 and with an obtuse angle relative to the vertical plane of side portion 113 at or near posterior region 120 of implant 100. As depicted, the vertical struts that form the planar truss of side portion 113 of external truss structure proximate posterior region 120 of implant 100 are shorter than struts that form side portion of external truss structure proximate anterior region 118 of implant 100. In the illustrated embodiment, in which the vertical trusses are substantially evenly spaced, the struts forming the "X" cross members of the side planar trusses proximate the posterior region 120 of implant 100 are shorter than struts forming the "X" cross members of the side planar trusses proximate the anterior region 118 of implant 100. Other embodiments may include variations in the arrangement of the trusses to provide various configurations of the implant. For example, in some embodiments only one or neither of the top and bottom external truss portions may be non-perpendicular to the side portions of the external truss proximate the anterior and posterior portions of the implant. Further, the side, top, and/or bottom portions may include multiple planar trusses angled relative to one another in any orientation. For example, the top or bottom portions may include four planar trusses, each formed of multiple truss units, such that the portion(s) includes a pyramidal like shape.

Figure 2D:
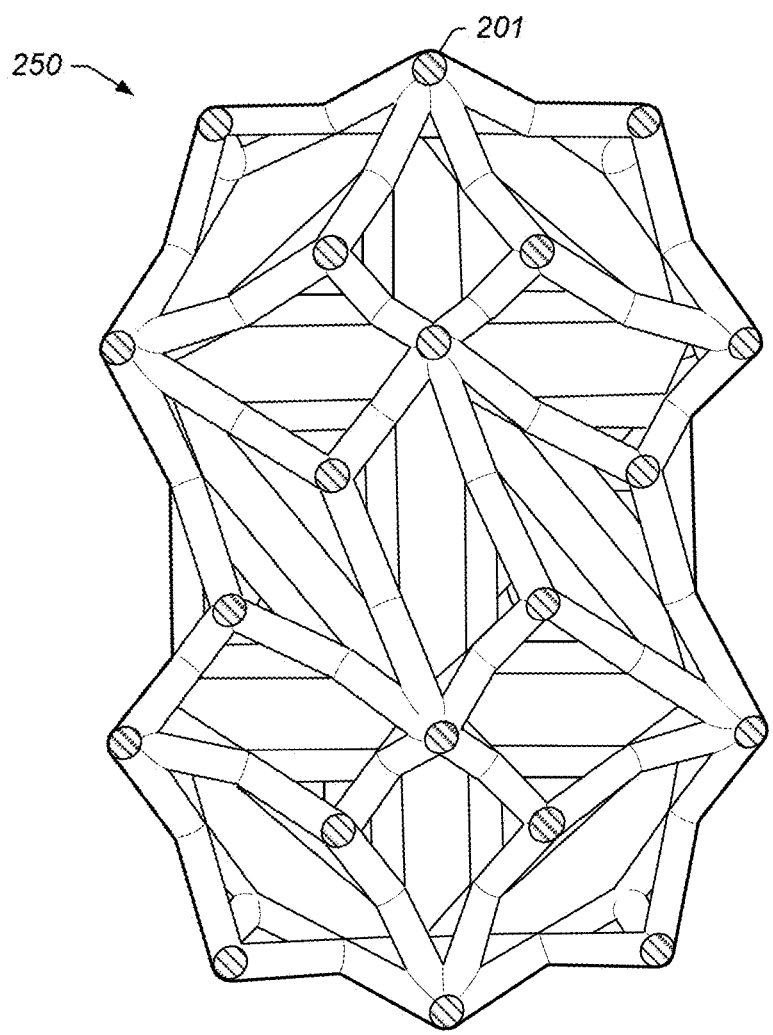

In some embodiments, the implant may not include lordosis. For example, FIGS. 2A-2B illustrate two views of an embodiment of an implant 200 without lordosis. In some embodiments, the top surface and bottom surface may not include connecting struts. For example, FIGS. 2C-2D illustrate two views of implant 250 without outer struts (e.g., without external truss portions formed of planar trusses). In the illustrated embodiment, implant 250 includes an internal web structure and does not include an external truss structure. For example, in the illustrated embodiment, the exterior faces of implant 250 are defined by a plurality of truss units that are angled relative to each of its adjacent truss units. The relative alignment of the truss units results in a non-planar exterior that includes a plurality of pointed junctions. The pointed junctions (e.g., pointed junction 201)

may operate to dig into the surrounding bone to hold the implant in place (for example, if the implant is being used in a corpectomy device).

Figure 5A:
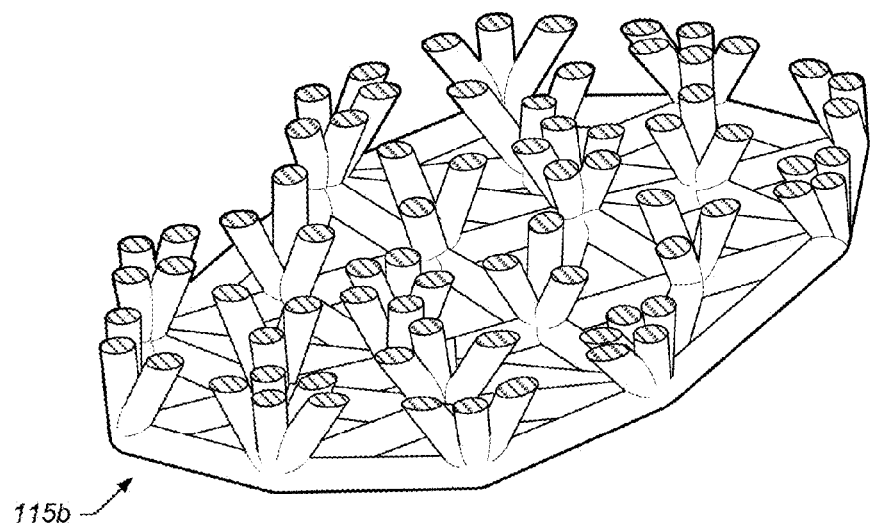
FIGS. 5A-5C illustrate progressive sectioned views of the implant showing the internal structure of the implant, according to an embodiment.
Figure 5B:
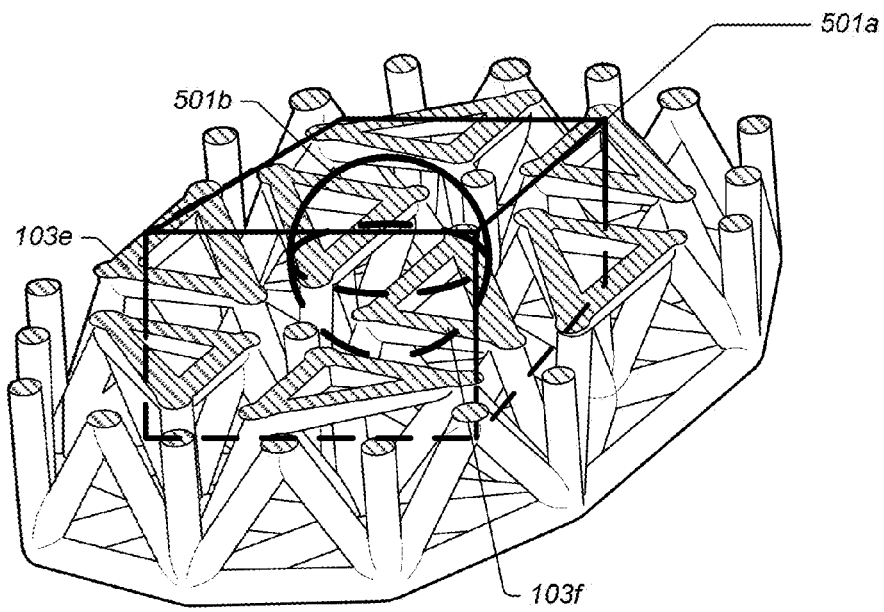
Figure 5C:
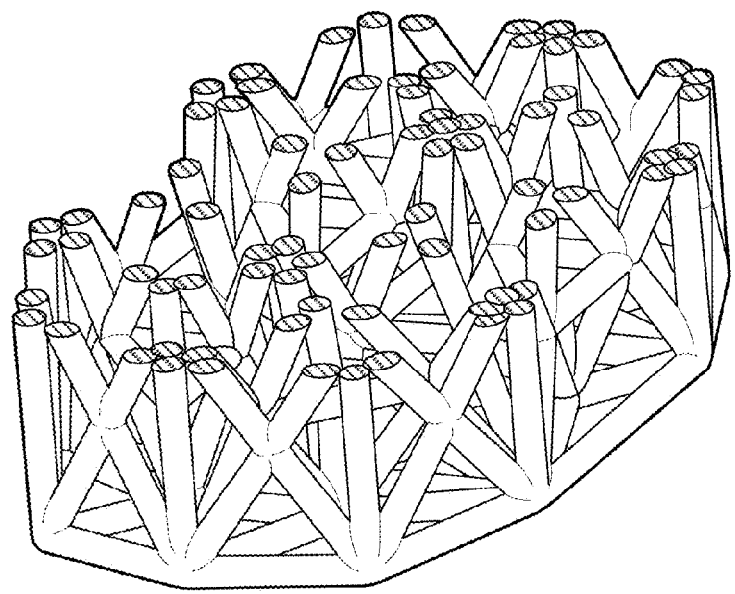
Figure 5D:
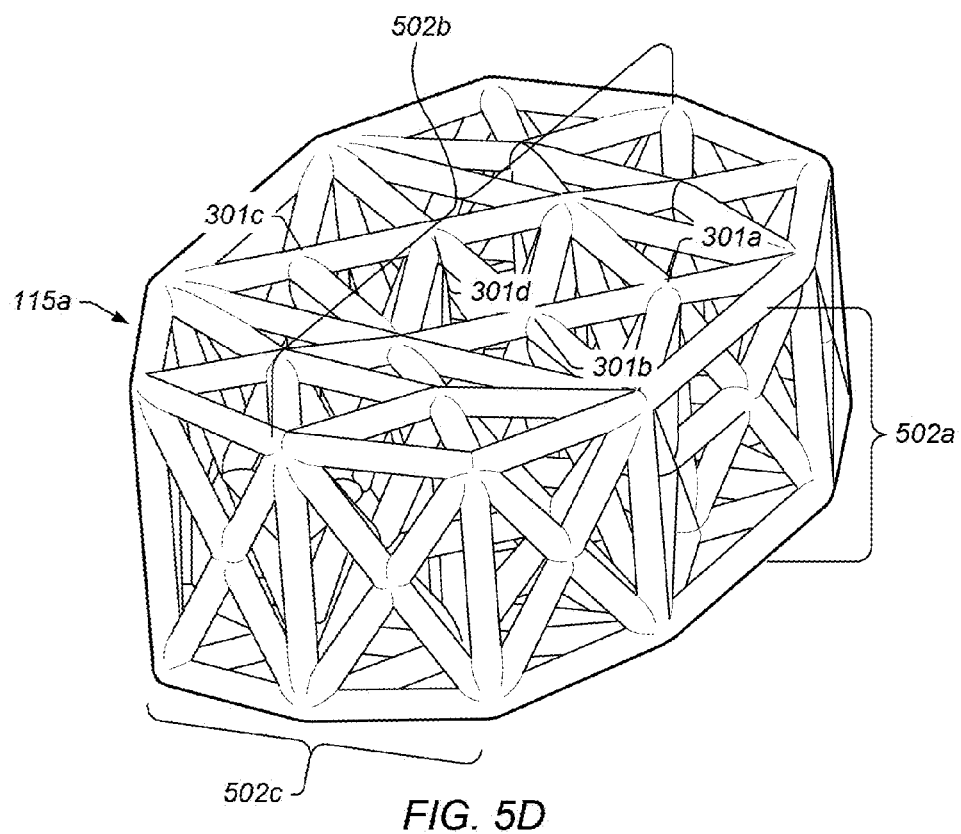
FIG. 5D illustrates an isometric view of the implant, according to an embodiment.

FIGS. 5A-5C illustrate progressive sectioned views of implant 100 showing the internal structure of implant 100, according to an embodiment. FIG. 5A illustrates a sectioned view of a lower portion of implant 100. Bottom surface 115b is shown with various struts (e.g., struts 103) extending upward from bottom surface 115b. FIG. 5B illustrates a sectioned view approximately mid-way through implant 100. Struts, such as struts 103e,f, shared by various stacked tetrahedrons in the web structure are shown. Some struts extend through central portion 501a and/or 501b of implant 100. FIG. 5B also shows central portions 501a,b of implant 100. In some embodiments, central portion 501a may include a rectangular region that has a width of approximately 50% of the implant width, a height of approximately 50% of the implant height, and a length of approximately 50% of the implant length and located in the center of implant 100. In some embodiments, central portion 501b may encompass a region (e.g., a spherical region, square region, etc.) of approximately a radius of approximately ⅛ to ¼ of the width of implant 100 around a position located approximately at one half the width, approximately one half the length, and approximately one-half the height of implant 100 (i.e., the center of implant 100). Other central portions are also contemplated. For example, the central portion may include a square region with a length of one of the sides of the square region approximately ¼ to ½ the width of implant 100 around a position approximately at one half the width, approximately one half the length, and approximately one half the height of the implant. An example height 502a, width 502b, and length 502c, is shown in FIG. 5D. In some embodiments, the height may be up to about 75 mm or more. In some embodiments, such as those used for long bone reconstruction, the width and/or length could be approximately 7 inches or longer. In some embodiments, the width, length, and/or height may vary along implant 100 (e.g., the height may vary if the implant includes lordosis). The height may be taken at one of the opposing sides, the middle, and/or may be an average of one or more heights along the length of implant 100. The web structure may extend through central portion 501a,b of the implant (e.g., at least one strut of the web structure may pass at least partially through central portion 501a,b). FIG. 5C illustrates another sectioned view showing sectioned views of top tetrahedrons in the web structure. FIG. 5D shows a complete view of implant 100 including top surface 115a with vertices 301a-d.

Figure 6A:
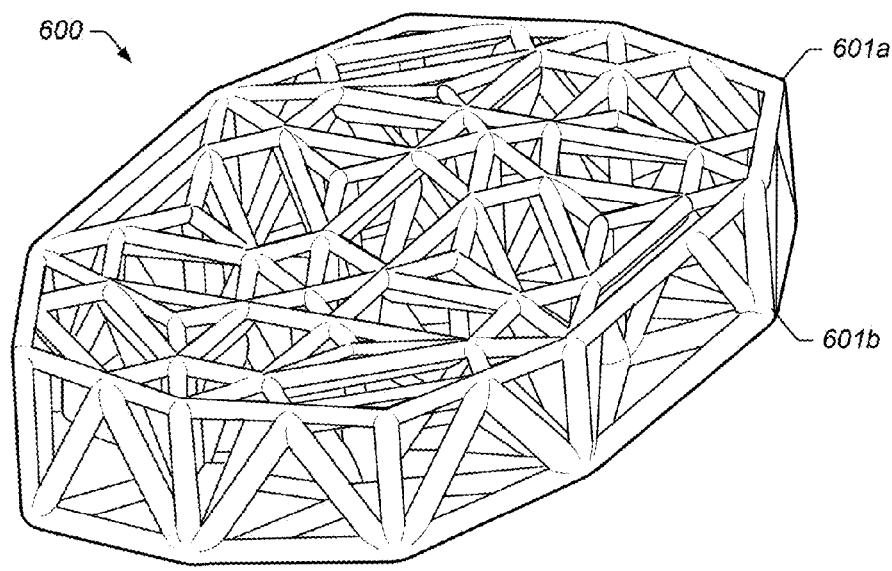
FIGS. 6A-6D illustrate another configuration of the web structure, according to an embodiment.
Figure 6B:
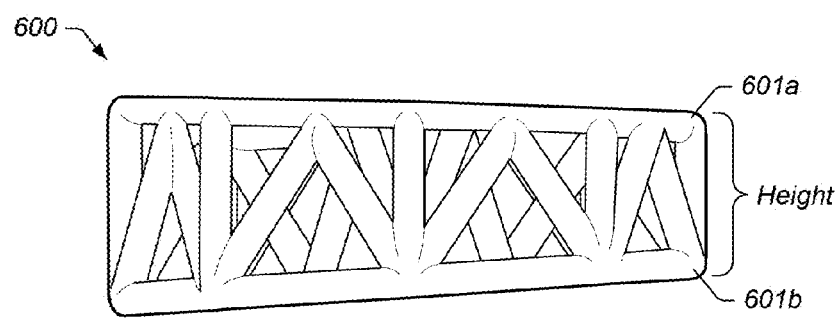

FIGS. 6A-6D illustrate alternate embodiments of an implant. In some embodiments, different sections of the hexahedron-shaped geometric design may be used. For example, as seen in FIG. 6A, the bottom half of the hexahedron-shaped geometric design may be used (primarily including the lower tetrahedron structures). If using the bottom half of the design, implant 600 may be expanded proportionately to have similar overall dimensions as the hexahedron-shaped geometric design (e.g., the tetrahedrons may be expanded to approximately twice the height of the tetrahedrons in the hexahedron-shaped geometric design to give implant 600 a height approximately the same as the hexahedron-shaped geometric design). In some embodiments, implant 600 may also be angled (e.g., on top surface 601a and/or bottom surface 601b) to provide implant 600 with lordosis to, in some embodiments, have a better fit between the vertebral endplates. Top surface 601a and/or bottom surface 601b may also include struts to connect nodes of implant 600 (e.g., see the strut network on the top surface in FIG. 6a). Other patterns of struts for top surface 601a and/or bottom surface 601b may also be used. In some embodiments, implant 600 may not include negative angles between struts and may thus be easier to create through a casting or molding process.

Figure 6C:
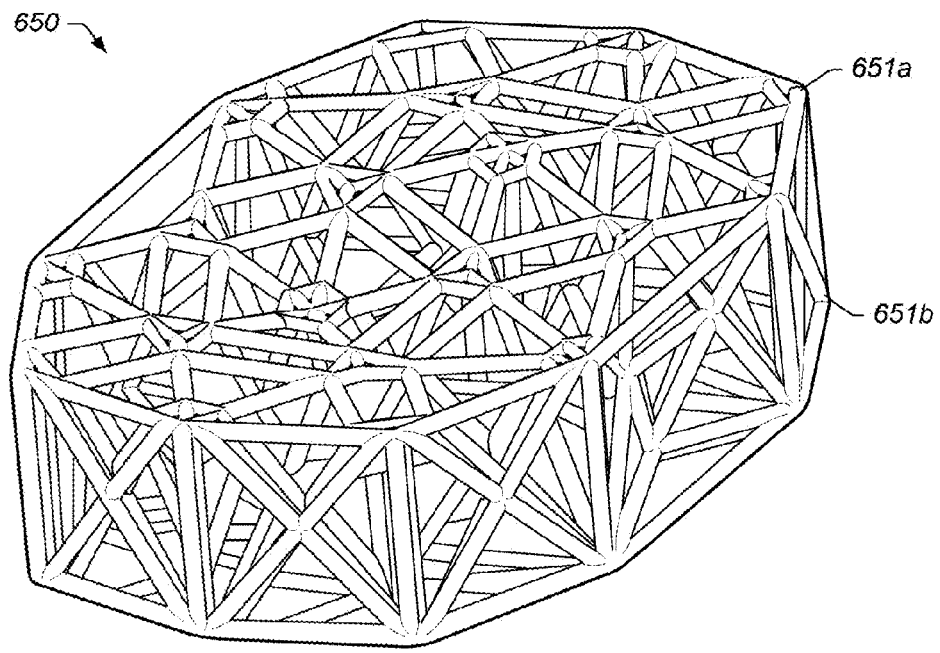
Figure 6D:
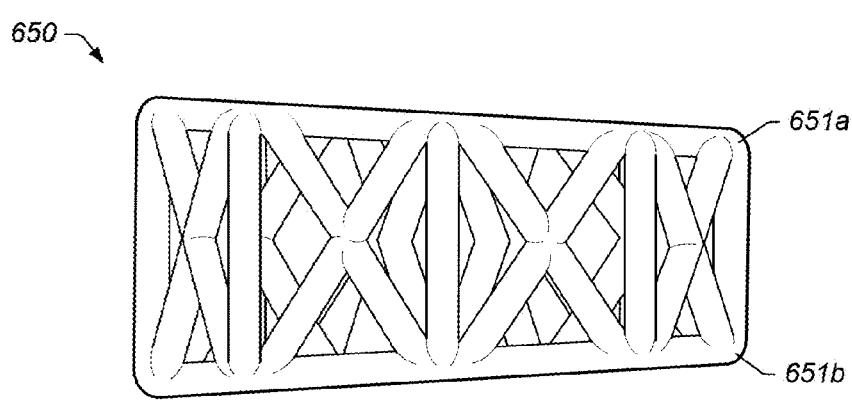

FIGS. 6C-6D illustrate another alternate embodiment of an implant. In some embodiments, approximately the middle 40 to 60 percent of the hexahedron-shaped geometric design may be used in implant 650. For example, if an overall height of the hexahedron-shaped geometric design is approximately 37 mm, approximately the bottom 10 mm and approximately the top 10 mm of the design may be removed and approximately the middle 17 mm of the design may be used for the implant. Middle portion of implant 650 may then be expanded proportionately such that the approximate height of the expanded design may be approximately 37 mm (or a different height as needed). Top surface 651a and bottom surface 651b may include a network of struts (e.g., see the struts on top surface 651a of FIG. 6C) (other networks of struts are also contemplated). Other portions of the design for the implant are also contemplated (e.g., the top half of the design shown in FIG. 1A, the bottom half of the design shown in FIG. 1A, etc). Design portions may be proportionately expanded to meet specified dimensions (e.g., specified height, width, and length). In some embodiments, the amount of struts may be reduced or material in the implant may be redistributed so that some struts may have a larger diameter and some may have a smaller diameter (e.g., the different diameters may reinforce against different directional forces). In some embodiments, a partial-design cage may be used (e.g., with half of the web structure so that the structure includes a tetrahedron. Further, in some embodiments, the implant may include angled surfaces (e.g., an angled top surface 651a and/or angled bottom surface 651b) to provide lordosis for implants to be implanted between the vertebral endplates.

In some embodiments, the web structure of an implant may distribute forces throughout the implant when implanted. For example, the connecting struts of the web structure may extend throughout the core of an implant, and the interconnectivity of struts may disperse the stress of compressive forces throughout implant to reduce the potential of stress risers (the distribution of forces throughout the implant may prevent concentration of stress on one or more portions of the vertebrae that may otherwise result in damage to the vertebrae).

In some embodiments, the web structure of an implant (e.g., the external and internal struts of the implant) may also provide surface area for bone graft fusion. For example, the web structure extending throughout an implant may add additional surface areas (e.g., on the surface of the struts making up the implant) to fuse to the bone graft material and prevent bone graft material from loosening or migrating from the implant. In some embodiments, the web structure may also support bone in-growth. For example, when implanted, adjacent bone (e.g., adjacent vertebrae if the implant is used as a spinal implant) may grow over at least a portion of struts of the implant. The bone growth and engagement between the bone growth and the implant may further stabilize the implant. In some embodiments, the surfaces of the implant may be formed with a rough surface to assist in bone in-growth adhesion.

In some embodiments, struts may have a diameter approximately in a range of about 0.025 to 5 millimeters (mm) (e.g., 1.0 mm, 1.5 mm, 3 mm, etc). Other diameters are also contemplated (e.g., greater than 5 mm). In some embodiments, the struts may have a length approximately in a range of 0.5 to 20 mm (e.g., depending on the implant size needed to, for example, fit a gap between vertebral endplates). As another example, struts may have a length approximately in a range of 30-40 mm for a hip implant. In some embodiments, the reduced strut size of the web structure may allow the open cells in implant 100 to facilitate bone growth (e.g., bone may grow through the open cells once implant 100 is implanted in the body). Average subsidence for implants may be approximately 1.5 mm within the first 3 weeks post op (other subsidence is also possible (e.g., approximately between 0.5 to 2.5 mm)). A strut size that approximately matches the subsidence (e.g., a strut size of approximately 1.5 mm in diameter and a subsidence of approximately 1.5 mm) may result in a net 0 impedance (e.g., the bone growth growing around the struts) after the implant has settled in the implanted position. The net 0 impedance throughout the entire surface area of the implant/vertebrae endplate interface may result in a larger fusion column of bone that may result in more stable fusion. Other fusion column sizes are also contemplated. The configuration of the implant may redistribute the metal throughout the implant. In some embodiments, a rim may not be included on the implant (in some embodiments, a rim may be included). The resulting bone growth (e.g., spinal column) may grow through the implant.

In some embodiments, greater than 50% of the interior volume of implant 100 may be open. In some embodiments, greater than 60%, greater than 70%, and/or greater than 80% of implant 100 may be open (e.g., 95%). In some embodiments, the open volume may be filled with bone growth material. For example, cancellous bone may be packed into an open/internal region of implant.

In some embodiments, at least a portion of the surfaces of the implant may be coated/treated with a material intend to promote bone growth and/or bone adhesion and/or an anitmicrobial agent to prevent infections. For example, in some embodiments, the surface of the struts may be coated with a biologic and/or a bone growth factor. In some embodiments, a biologic may include a coating, such as hydroxyapatite, bone morphogenetic protein (BMP), insulinlike growth factors I and II, transforming growth factor-beta, acidic and basic fibroblast growth factor, platelet-derived growth factor, and/or similar bone growth stimulant that facilitates good biological fixation between the bone growth and a surface of the implant. In some embodiments, a bone growth factor may include a naturally occurring substance capable of stimulating cellular growth, proliferation and cellular differentiation (e.g., a protein or steroid hormone). In some embodiments, the surface of the implant (e.g., the struts, the external truss structure, etc.) may be coated with collagen.

In some embodiments, a biologic and/or growth factor may be secured to a central region of an implant. For example, in some embodiments, a biologic or growth factor may be provided on at least a portion of a strut that extends through central portion 501a and/or 501b of implant 100, see FIG. 5B. Such an embodiment may enable the delivery of a biologic and or a growth factor to a central portion of an implant. For example, the biologic or growth factor may be physically secured to a strut in a central portion of the implant as opposed to being packed into an open volume that does not include a strut provided therein for the physical attachment of the biologic and/or growth factor.

As the implant settles into the implant site, subsidence may place additional pressure on the bone graft material (which may already be under compressive forces in the implant) and act to push the bone graft material toward the sides of the implant (according to Boussinesq's theory of adjacent material, when a force is applied to a member that is adjacent to other materials (such as sand, dirt, or bone graft material) the force against the member creates a zone of increased pressure (e.g., 60 degrees) in the adjacent material). Struts of the implant may resist bone graft material protrusion from the sides of the web structure and may increase the pressure of the bone graft material. Bone graft material may need to be implanted in a higher-pressure environment to create an environment conducive to strong bone growth (e.g., according to Wolf's law that bone in a healthy person or animal will adapt to the loads it is placed under). The web structure may thus increase the chance of stronger fusion.

Web structures formed from other truss configurations are also contemplated. For example, the trusses may include a series of packing triangles, a two-web truss, a three-web truss, etc. Further, the web structure for an implant may include one or more trusses as described in U.S. Pat. No. 6,931,812 titled "Web Structure and Method For Making the Same", which issued Aug. 23, 2005, which is hereby incorporated by reference in its entirety as though fully and completely set forth herein.

Figure 8:
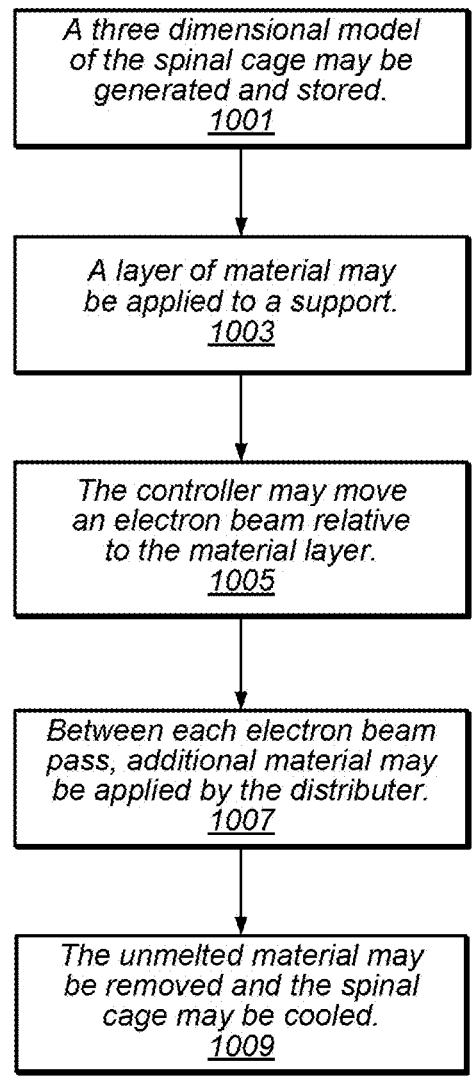
FIG. 8 illustrates a flowchart of a method for making an implant, according to an embodiment.

FIG. 8 illustrates a flowchart of a method for making an implant. In some embodiments, an implant may be made through rapid prototyping (e.g., electron beam melting, laser sintering, etc). It should be noted that in various embodiments of the methods described below, one or more of the elements described may be performed concurrently, in a different order than shown, or may be omitted entirely. Other additional elements may also be performed as desired. In some embodiments, a portion or the entire method may be performed automatically by a computer system.

At 1001, a three dimensional model of an implant is generated and stored in a storage medium accessible to a controller operable to control the implant production process. At 1003, a layer of material (e.g., a powder, liquid, etc.) is applied to a support. In some embodiments, the powder may include γTiAl (γTitanium Aluminides) which may be a high strength/low weight material. Other materials may also be used. The powder may be formed using a gas atomization process and may include granules with diameters approximately in a range of 20 to 200 micrometers (μm) (e.g., approximately 80 μm). The powder may be delivered to the support through a distributer (e.g., delivered from a storage container). The distributer and/or the support may move during distribution to apply a layer (e.g., of powder) to the support. In some embodiments, the layer may be approximately a uniform thickness (e.g., with an average thickness of 20 to 200 micrometers (μm)). In some embodiments, the distributer and support may not move (e.g., the material may be sprayed onto the support). At 1005, the controller moves an electron beam relative to the material layer. In some embodiments, the electron beam generator may be moved, and in some embodiments the support may be moved. If the material is γTiAl, a melting temperature approximately in a range of 1200 to 1800 degrees Celsius (e.g., 1500 degrees Celsius) may be obtained between the electron beam and the material. At 1007, between each electron beam pass, additional material may be applied by the distributer. At 1009, the unmelted material is removed and the implant cooled (e.g., using a cool inert gas). In some embodiments, the edges of the implant may be smoothed to remove rough edges (e.g., using a diamond sander). In some embodiments, the implant may include rough edges to increase friction between the implant and the surrounding bone to increase adhesion of the implant to the bone.

Other methods of making an implant are also contemplated. For example, an implant may be cast or injection molded. In some embodiments, multiple parts may be cast or injection molded and joined together (e.g., through welding, melting, etc). In some embodiments, individual struts forming the implant may be generated separately (e.g., by casting, injection molding, etc.) and welded together to form the implant. In some embodiments, multiple implants of different sizes may be constructed and delivered in a kit. A medical health professional may choose an implant (e.g., according to a needed size) during the surgery. In some embodiments, multiple implants may be used at the implant site.

Specialized tools may be used to insert the implants described herein. Examples of tools that may be used are described in U.S. Published Patent Applications Nos.: 2010/0161061; 2011/0196495; 20110313532; and 2013/0030529, each of which is incorporated herein by reference.

Figure 9:
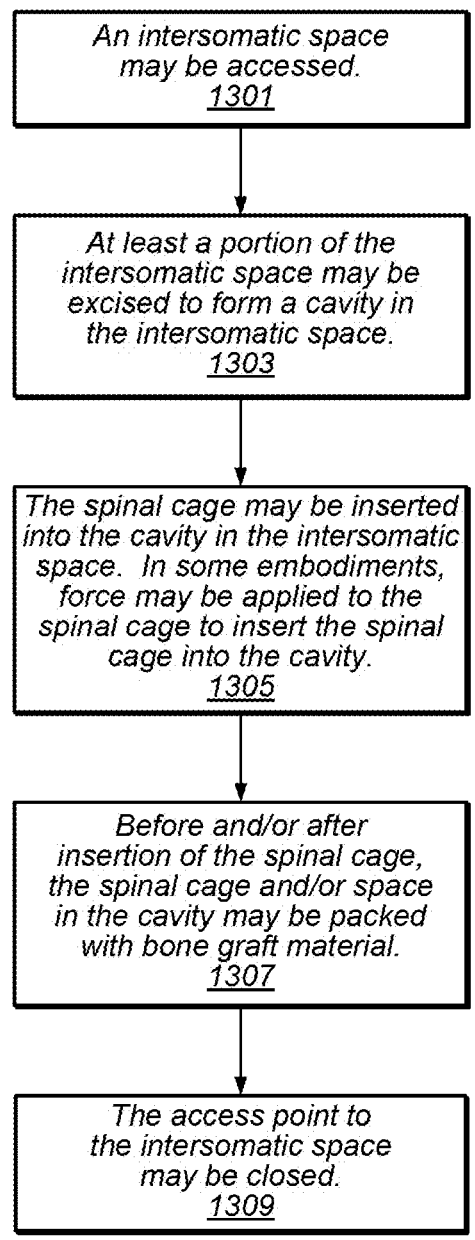
FIG. 9 illustrates a flowchart of a method for implanting a spinal implant, according to an embodiment.

FIG. 9 illustrates a flowchart of a method for implanting a spinal implant, according to an embodiment. It should be noted that in various embodiments of the methods described below, one or more of the elements described may be performed concurrently, in a different order than shown, or may be omitted entirely. Other additional elements may also be performed as desired. In some embodiments, a portion or the entire method may be performed automatically by a computer system.

At step 1301, an intersomatic space is accessed. For example, an anterior opening may be made in a patient's body for an anterior lumbar inter-body fusion (ALIF) approach or a posterior opening may be made for a posterior lumbar inter-body fusion (PLIF) approach. At 1303, at least a portion of the intersomatic space is excised to form a cavity in the intersomatic space. At 1305, the implant is inserted into the cavity in the intersomatic space. In some embodiments, a handler, or some other device, is used to grip the implant. In some embodiments, a force may be applied to the implant (e.g., through a hammer) to insert the implant into the cavity. At 1307, before and/or after insertion of the implant, the implant and/or space in the cavity may be packed with bone graft material. At 1309, the access point to the intersomatic space may be closed (e.g., using sutures).

In some embodiments, the implant may be customized. For example, three dimensional measurements and/or shape of the implant may be used to construct an implant that distributes the web structure throughout a three-dimensional shape design.

In some embodiments, a truss/web structure may be disposed on at least a portion of an implant to facilitate coupling of the implant to an adjacent structure. For example, where an implant is implanted adjacent a bony structure, one or more truss structures may be disposed on and/or extend from a surface (e.g., an interface plate) of the implant that is intended to contact, and at least partially adhere to, the bony structure during use. In some embodiments, such as those including an intervertebral implant disposed between the end plates of two adjacent vertebrae during, one or more truss structures may be disposed on a contact surface of the intervertebral implant to facilitate bone growth that enhances coupling of the intervertebral implant to the bony structure. For example, a truss structure may include one or more struts that extend from the contact surface to define an open space for bone growth therethrough, thereby enabling bone through growth to interlock the bone structure and the truss structure with one another to couple the implant to the bony structure at or near the contact face. Such interlocking bone through growth may inhibit movement between the implant and the bony structure which could otherwise lead to loosening, migration, subsidence, or dislodging of the implant from the intended position. Similar techniques may be employed with various types of implants, including those intended to interface with tissue and/or bone structures. For example, a truss structure may be employed on a contact surface of knee implants, in a corpectomy device, in a hip replacement, in a knee replacement, in a long bone reconstruction scaffold, or in a cranio-maxifacial implant hip implants, jaw implant, an implant for long bone reconstruction, foot and ankle implants, shoulder implants or other joint replacement implants or the like to enhance adherence of the implant to the adjacent bony structure or tissue. Examples of truss structures, and other structures, that may extend from the surface of an implant to facilitate coupling of the implant to an adjacent structure are described in U.S. Published Patent Application No. 2011/0313532, which is incorporated herein by reference.

While implants described herein are depicted as being composed of substantially straight struts, it should be understood that the struts can be non-linear, including, but not limited to curved, arcuate and arch shaped. Examples of implants having non-linear struts are described in U.S. patent application Ser. No. 13/668,968, which is incorporated herein by reference.

It is known that osteoblasts under an appropriate load produce bone morphogenetic protein ("BMP"). BMPs are a group of growth factors also known as cytokines and as metabologens. BMPs act as morphogenetic signals that signal the formation of bone (i.e., an osteogenetic response). Thus, by increasing the production of one or more BMPs the osteogentic response to an implant is increased, creating an implant that is integrated into the newly formed bone.

Figure 10:
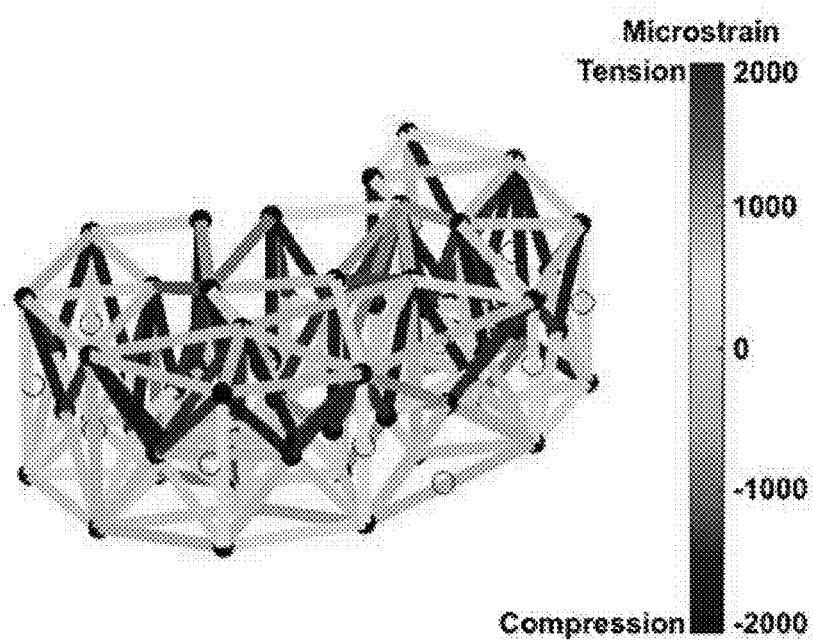
FIG. 10 depicts a diagram of stresses distributed through an implant.
Figure 11A:
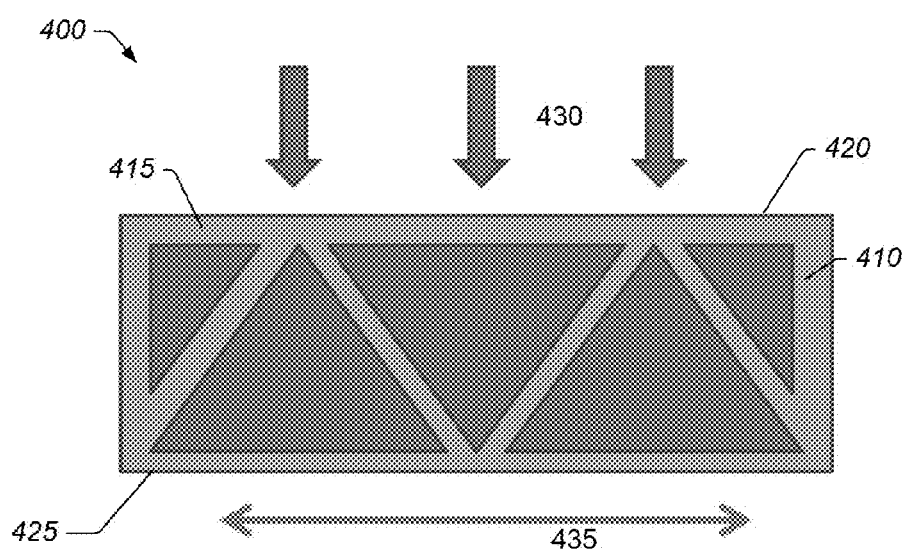
FIGS. 11A-C depict schematic diagrams of the effect of compression on osteoblast cells.
Figure 11B:
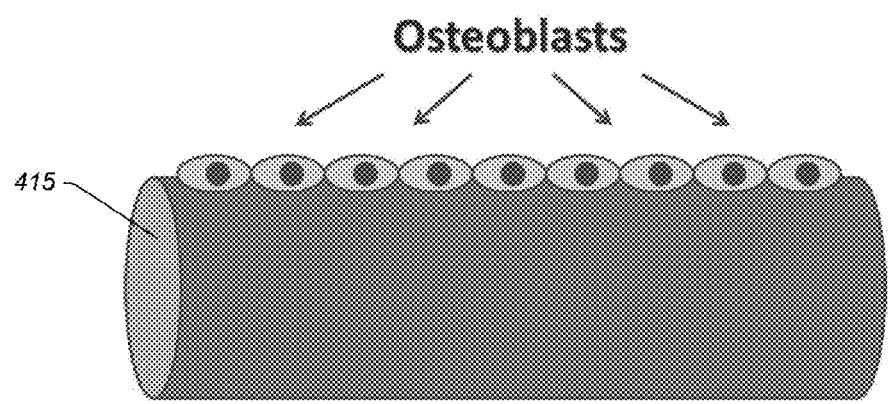
Figure 11C:
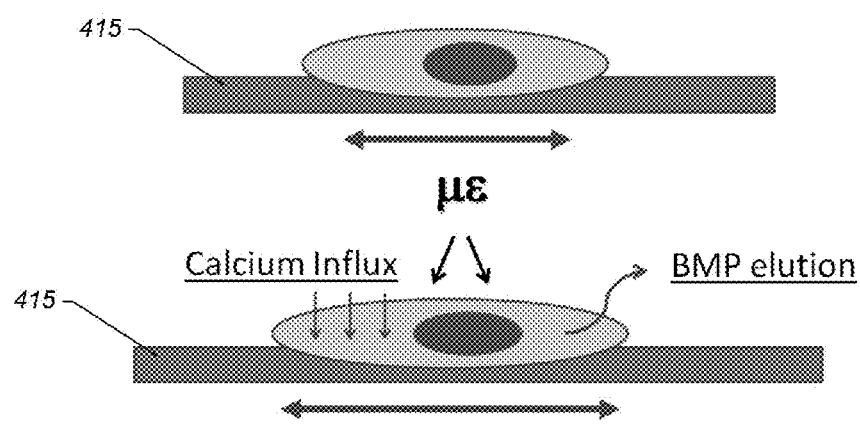

A web structure that includes a plurality of joined truss units exhibits a number of deformations in response to loading. FIG. 10 below depicts some of the forces that are dispersed along the struts of the truss units that make up the web structure. When used as a bone implant, web structures as described herein may promote the growth of bone in and around the web structure, in part, because of the enhanced BMP production. As shown in FIGS. 11A-C, osteoblasts become attached to the struts of a web structure. Under loading, the micro strain in the struts causes localized deformation which in turn transfers the strain to the adhered osteoblasts which cause the osteoblasts to elute BMP.

FIG. 11A depicts a schematic diagram of an implant 400 that includes a space truss 410. Bone structures, not shown, are typically disposed against a top face 420 and a bottom face 425 of implant 400. During use, the stress from the contacting bone structures (denoted by arrows 430) can cause implant 400 to lengthen (denoted by arrow 435) as the implant is compressed. This lengthening can have a beneficial effect on the formation of BMP by osteoblasts that adhere to the implant. Adjacent bone adds compression forces to the slanted struts. This compression may lead to bone remodeling. The combination of the two forces (compression and lengthening) creates bone growth/remodeling which leads to accelerated healing and achieving a mature fusion in a shorter amount of time as compared to predicate devices.

FIG. 11B depicts a close-up view of strut 415 of implant 400. Strut 415, in FIG. 11B is shown in a non-elongated state. This may represent the state of strut 415 when the implant is not under load from the contacting bone structures. Osteoblasts are depicted as adhered to strut 415. The osteoblasts are shown in their normal, non-elongated form. FIG. 11C depicts strut 415 in an elongated state, which exists when the bone structures are applying a compressive force to implant 400. As shown, the osteoblasts are believed to be stretched due to the elongation of strut 415. Elongation of the osteoblasts lead to an influx of calcium which is then converted into BMP and eluted back out. Studies have shown that the creating a microstrain in the osteoblasts of between 500με and 2000με or between about 1000με and about 1500με enhances the production of BMP. Alternatively, the production of BMP may be attained when the length of the attached osteoblasts is changed between about 0.05% and about 0.2% or between about 0.1% and about 0.15%. Configuring a truss system to intentionally create lengthening/microstrain in osteoblasts may reduce the time needed for the bone structure to be repaired.

In an embodiment, an implant for interfacing with a bone structure includes a web structure comprising a plurality of struts joined at nodes. The web structure is configured to interface with human bone tissue. In one embodiment, a diameter and/or length of the struts are predetermined such that when the web structure is in contact with the bone structure, BMP production from osteoblasts adhering to the implant surface is achieved. In one embodiment, the diameter and/or length of the struts is predetermined so that at least a portion of the struts create a microstrain in the adhered osteoblasts of between about 1 and 5000 microstrain, 500με and about 2000με or between about 1000με and about 1500με. In an embodiment, the diameter and/or length of the struts is predetermined so that at least a portion of the struts create a change in length of the adhered osteoblasts of between about 0.05% and about 0.2% or between about 0.1% and about 0.15%.

An implant may be prepared having struts of a length of between about 1 to 100 mm. The diameter of the struts may be set such that the strut undergoes a change of length of between about 0.05% and 0.2% when the web structure is in contact with the bone structure. In some embodiments, the diameter of the struts is predetermined such that the strut undergoes a change of length of between about 0.000125% and 0.0005% or between about 0.00025% and 0.000375%.

Any implant described herein may be modified so that at least a portion of the struts the form the web structure produce the appropriate microstrain/lengthening of adhered osteoblasts. In some embodiments, most if not all of the struts that form the web structure of an implant may be 'programmed' (or designed) to stimulate BMP production. In other embodiments, some struts may be programmed/designed for BMP production, while other struts have different physical properties than the programmed struts.

An implant may be optimized to distribute stresses encountered by the implant. Most implants used for bone repair are placed in locations that apply non-uniform stress to the implant. The non-uniform stress creates different forces across the implant. If an implant is designed to withstand a certain homogenous force, the implant may fail when subjected to non-uniform stress. In a non-uniform stress situation, some of the stress on the implant may be sufficient to deform the implant. It is desirable to have an implant that is customized to the expected non-uniform stress that will be encountered in the bone structure being repaired.

In an embodiment, an implant for interfacing with a bone structure, includes a web structure having a plurality of struts joined at nodes. The web structure is configured to interface with human bone tissue, and has a first bone contact surface and a second bone contact surface. A first portion of struts that are part of the space truss have a physical property that is different from a second portion of the struts that are a part of the space truss. In this manner an implant may be created which optimizes the stresses encountered by the implant to help inhibit failure of the implant.

In one embodiment, the first portion of struts that are part of the space truss have a deformation strength that is different from a second portion of the struts that are a part of the space truss. The space truss may include one or more central struts extending from the first bone contact surface to the second bone contact surface. The central struts may have a deformation strength that is greater than or less than the surrounding struts, depending on the location of the implant. The space truss may include one or more longitudinal struts extending parallel to the first bone contact surface and/or the second bone contact surface, wherein the longitudinal struts have a deformation strength that is greater than or less than the surrounding struts.

The physical properties of the struts of the implant may be varied such that the diameter of the first portion of the struts is greater than a diameter of the second portion of the struts. In some embodiments, the first portion of struts are formed from a material that is different from the material used to form the second portion of struts. In some embodiments, the first portion of struts have a diameter that is different from the diameter of the second portion of struts. In some embodiments, the first portion of struts have a density that is different from the density of the second portion of struts. In some embodiments, he first portion of struts have a porosity that is different from the porosity of the second portion of struts. Any combination of these different physical properties may be present in an implant to help optimize the distribution of stress throughout the implant.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

In accordance with the above descriptions, in various embodiments, an implant may include a web structure. The web structure for the implant may include a micro truss design. In some embodiments, the micro truss design may include a web structure with multiple struts. Other web structures are also contemplated. The web structure may extend throughout the implant (including a central portion of the implant). The web structure may thus reinforce the implant along multiple planes (including internal implant load bearing) and provide increased area for bone graft fusion. The web structure may be used in implants such as spinal implants, corpectomy devices, hip replacements, knee replacements, long bone reconstruction scaffolding, and cranio-maxillofacial implants foot and ankle, hand and wrist, shoulder and elbow (large joint, small joint, extremities). Other implant uses are also contemplated. In some embodiments, the web structure for the implant may include one or more geometric objects (e.g., polyhedrons). In some embodiments, the web structure may not include a pattern of geometrical building blocks (e.g., an irregular pattern of struts may be used in the implant). In some embodiments, the web structure may include a triangulated web structure including two or more tetrahedrons. A tetrahedron may include four triangular faces in which three of the four triangles meet at each vertex. The web structure may further include two tetrahedrons placed together at two adjacent faces to form a web structure with a hexahedron-shaped frame (including six faces). In some embodiments, multiple hexahedron-shaped web structures may be arranged in a side-by-side manner. The web structures may connect directly through side vertices (e.g., two or more hexahedron-shaped web structures may share a vertex). In some embodiments, the web structure may be angled to provide lordosis to the implant.

Further modifications and alternative embodiments of various aspects of the invention may be apparent to those skilled in the art in view of this description. For example, although in certain embodiments, struts have been described and depicts as substantially straight elongated members, struts may also include elongated members curved/arched along at least a portion of their length. Accordingly, this description is to be construed as illustrative only and is for the purpose of teaching those skilled in the art the general manner of carrying out the invention. It is to be understood that the forms of the invention shown and described herein are to be taken as embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims. Furthermore, it is noted that the word "may" is used throughout this application in a permissive sense (i.e., having the potential to, being able to), not a mandatory sense (i.e., must). The term "include", and derivations thereof, mean "including, but not limited to". As used in this specification and the claims, the singular forms "a", "an" and "the" include plural referents unless the content clearly indicates otherwise. Thus, for example, reference to "a strut" includes a combination of two or more struts. The term "coupled" means "directly or indirectly connected".

What is claimed is:

1. A spinal implant for interfacing with a bone structure of a subject's spine, comprising:
    a web structure comprising a plurality of struts joined at nodes to form a space truss comprising a plurality of planar truss units, wherein the web structure is configured to interface with bone tissue, and wherein the plurality of planar truss units are coupled to one another such that one or more planar truss units lie in a plane that is not substantially parallel to a plane of a planar truss unit that shares at least one strut with the one or more planar truss units;
    wherein a diameter and/or length of the struts and/or density of the web structure are predetermined such that when the web structure is in contact with the bone at least a portion of the struts create a microstrain in adhered osteoblasts, bone matrix, or lamellar tissue; and
    wherein the implant has a shape and size that allows the implant to be implanted in between vertebrae of the subject's spine.

2. The implant of claim 1, where in the diameter and/or length of the struts and/or density of the web structure is predetermined so that the struts, under load, create a microstrain, in adhered osteoblasts, bone matrix, or lamellar tissue, wherein the microstrain is within a range that stimulates an osteogenetic response.

3. The implant of claim 1, wherein the diameter and/or length of the struts and/or density of the web structure is predetermined so that at least a portion of the struts create a microstrain in the adhered osteoblasts, bone matrix, or lamellar tissue of between about 1με and about 5000με.

4. The implant of claim 1, wherein the diameter and/or length of the struts and/or density of the web structure is predetermined so that at least a portion of the struts create a microstrain in the adhered osteoblasts, bone matrix, or lamellar tissue of between about 500με and about 2000με.

5. The implant of claim 1, wherein the diameter and/or length and/or density of the web structure of the struts is predetermined so that at least a portion of the struts create a microstrain in the adhered osteoblasts, bone matrix, or lamellar tissue of between about 1000με and about 1500με.

6. The implant of claim 1, wherein the diameter and/or length and/or density of the web structure of the struts is predetermined so that at least a portion of the struts create a change in length of the adhered osteoblasts of between about 0.05% and about 0.2%.

7. The implant of claim 1, wherein the diameter and/or length and/or density of the web structure of the struts is predetermined so that at least a portion of the struts create a change in length of the adhered osteoblasts of between about 0.1% and about 0.15%.

8. The implant of claim 1, wherein the struts have a length of between about 1 mm to about 100 mm, and wherein a diameter of the strut is predetermined such that the struts create a change in length of the adhered osteoblasts of between about 0.05% and 0.2% when the web structure is in contact with the bone structure.

9. The implant of claim 1, wherein the diameter of the strut is predetermined such that the strut undergoes a change of length of between about 0.000125% and 0.0005%.

10. The implant of claim 1, wherein the diameter of the strut is predetermined such that the strut undergoes a change of length of between about 0.00025% and 0.000375%.

11. The implant of claim 1, wherein one or more of the planar truss units comprise one or more planar triangular truss units having three substantially straight struts and three nodes in a triangular configuration.

12. The implant of claim 1, wherein one or more of the planar truss units comprises a first planar triangular truss unit coupled to a second planar triangular truss unit, wherein the first and second planar triangular truss units are coupled in an opposing manner with a single node defining the apex of each planar triangular truss unit.

13. The implant of claim 1, wherein a diameter of the struts of the web structure are predetermined such that when the web structure is in contact with the bone at least a portion of the struts create a microstrain in adhered osteoblasts, bone matrix, or lamellar tissue.

14. The implant of claim 1, wherein a length of the struts of the web structure are predetermined such that when the web structure is in contact with the bone at least a portion of the struts create a microstrain in adhered osteoblasts, bone matrix, or lamellar tissue.

15. The implant of claim 1, wherein a density of the web structure is predetermined such that when the web structure is in contact with the bone at least a portion of the struts create a microstrain in adhered osteoblasts, bone matrix, or lamellar tissue.

16. A method of repairing a bone structure in a subject's spine, comprising:
    obtaining an implant, the implant comprising:

a web structure comprising a plurality of struts joined at nodes to form a space truss comprising a plurality of planar truss units, wherein the web structure is configured to interface with bone tissue, and wherein the plurality of planar truss units are coupled to one another such that one or more planar truss units lie in a plane that is not substantially parallel to a plane of a planar truss unit that shares at least one strut with the one or more planar truss units;

wherein a diameter and/or length of the struts and/or density of the web structure are predetermined such that when the web structure is in contact with the bone at least a portion of the struts create a microstrain in adhered osteoblasts, bone matrix, or lamellar tissue; and placing the implant in between vertebrae of the subject's spine.

17. The method of claim 16, wherein the diameter and/or length of the struts and/or density of the web structure is predetermined so that at least a portion of the struts create a microstrain in the adhered osteoblasts, bone matrix, or lamellar tissue of between about 1µε and about 5000µε.

18. The method of claim 16, wherein the diameter and/or length and/or density of the web structure of the struts is predetermined so that at least a portion of the struts create a change in length of adhered osteoblasts of between about 0.05% and about 0.2%.

19. The method of claim 16, wherein the diameter of the strut is predetermined such that the strut undergoes a change of length of between about 0.000125% and 0.0005%.

20. The method of claim 16, wherein one or more of the planar truss units comprise one or more planar triangular truss units having three substantially straight struts and three nodes in a triangular configuration.

21. The method of claim 16, wherein one or more of the planar truss units comprises a first planar triangular truss unit coupled to a second planar triangular truss unit, wherein the first and second planar triangular truss units are coupled in an opposing manner with a single node defining the apex of each planar triangular truss unit.

22. The method of claim 16, wherein a diameter of the struts of the web structure are predetermined such that when the web structure is in contact with the bone at least a portion of the struts create a microstrain in adhered osteoblasts, bone matrix, or lamellar tissue.

23. The method of claim 16, wherein a length of the struts of the web structure are predetermined such that when the web structure is in contact with the bone at least a portion of the struts create a microstrain in adhered osteoblasts, bone matrix, or lamellar tissue.

24. The method of claim 16, wherein a density of the web structure is predetermined such that when the web structure is in contact with the bone at least a portion of the struts create a microstrain in adhered osteoblasts, bone matrix, or lamellar tissue.

* * * * *